Figure 1:
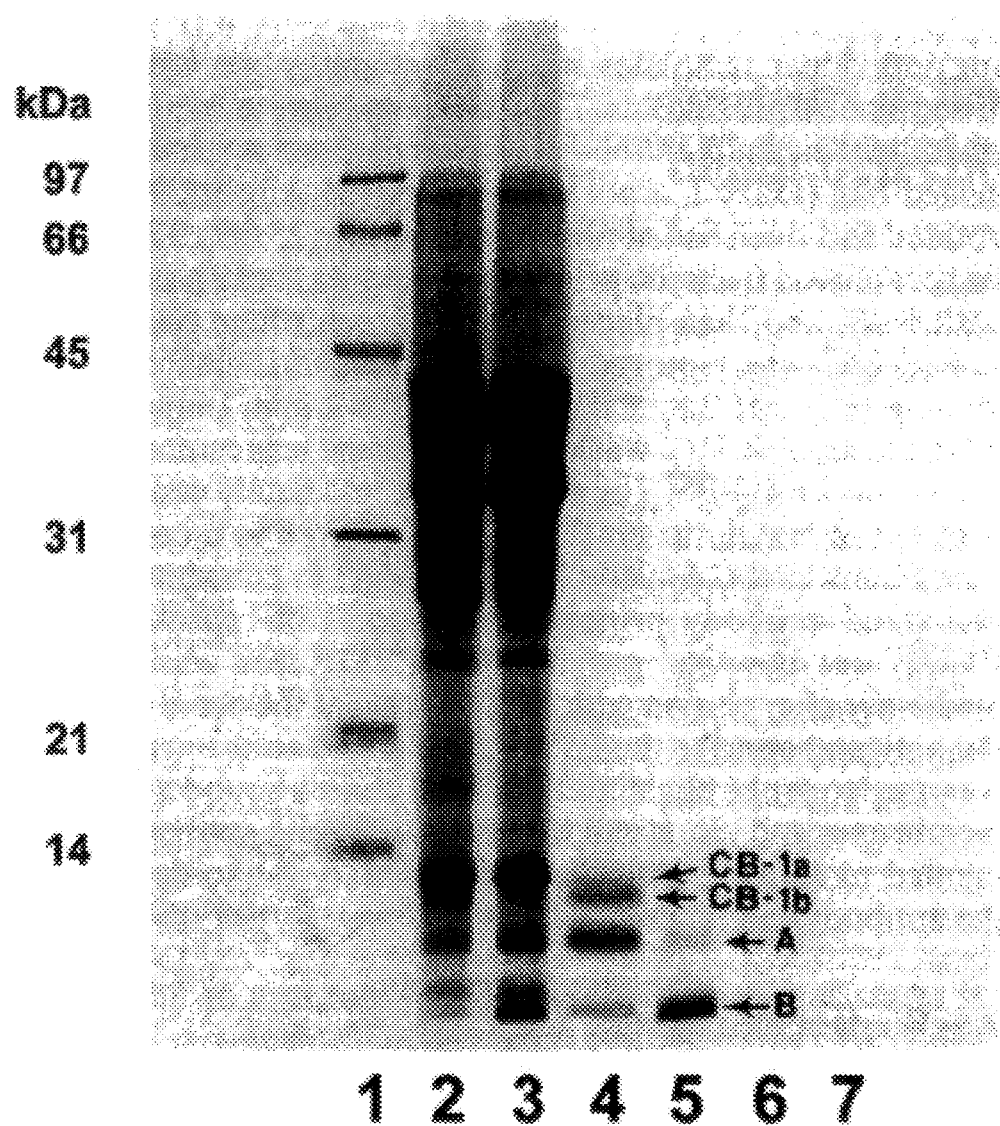

United States Patent [19]

Bausher

[11] Patent Number: 5,650,151
[45] Date of Patent: Jul. 22, 1997

[54] CITRUS PROTEINS FOR USE IN FIELD DETECTION OF CITRUS BLIGHT USING IMMUNOLOGICAL TECHNIQUES

[75] Inventor: Michael G. Bausher, Winter Park, Fla.

[73] Assignee: The United States of America as represented by the Secretary of Agriculture, Washington, D.C.

[21] Appl. No.: 369,566

[22] Filed: Jan. 6, 1995

Related U.S. Application Data

[63] Continuation of Ser. No. 792,508, Nov. 12, 1991.
[51] Int. Cl.$^6$ .............. A61K 39/00; A61K 39/35; C07K 14/415; C07K 16/16
[52] U.S. Cl. .................. 424/185.1; 424/184.1; 424/276.1; 530/370; 530/388.5; 530/389.1
[58] Field of Search ................ 424/184.1, 185.1, 424/276.1; 530/370, 388.5, 389.1

[56] References Cited

PUBLICATIONS

Derrick et al. Plant Disease, 74, 168–170.
Harlow et al. in Antibodies a Laboratory Manual pp. 66–67 Cold Spring Harbor Press 1988.
"Proteins Associated with Citrus Blight".
Bausher, M.G. Electrophonesis 11: 830–834, 1990 (Feb.).
Bausher et al. Plant Disease 75: 447–450, 1991 (May).
Derrick et al. Plant Disease 74(2) 168–170 (1990).
Harlsow et al. in "Antibody : A Laboratory Manual" pp. 55–76, CSH (1988).

*Primary Examiner*—Michael P. Woodward
*Assistant Examiner*—Jay Williams
*Attorney, Agent, or Firm*—M. Howard Silverstein; Joseph A. Lipovsky; John D. Fado

[57] ABSTRACT

The present invention relates to purified and isolated citrus blight, antigens and antibodies thereto leaf proteins which are specific indicators of the presence of citrus blight. The isolated and purified citrus blight leaf proteins are extracted from citrus blighted leaves and have a molecular weight of about 10,000 to about 30,00 daltons.

12 Claims, 13 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 16 amino acids
( B ) TYPE: amino acid
( D ) TOPOLOGY: linear ( i i ) MOLECULE TYPE: protein ( v ) FRAGMENT TYPE: internal ( x i ) SEQUENCE DESCRIPTION: SEQ ID NO:1:

```
Gly Glu Gly Thr Ala Thr Phe Tyr Thr Pro Pro Tyr Val Pro Ser Ala
1               5                   10                  15
```

( 2 ) INFORMATION FOR SEQ ID NO:2:

( i ) SEQUENCE CHARACTERISTICS:
( A ) LENGTH: 19 amino acids
( B ) TYPE: amino acid
( D ) TOPOLOGY: linear ( i i ) MOLECULE TYPE: protein ( v ) FRAGMENT TYPE: internal ( x i ) SEQUENCE DESCRIPTION: SEQ ID NO:2:

```
Val Asn Ala Val Ala Val Ile Thr Gly Asn Asn Gly Arg Lys Gly Thr
1               5                   10                  15

Val Ser Gly
```

( 2 ) INFORMATION FOR SEQ ID NO:3:

( i ) SEQUENCE CHARACTERISTICS:
( A ) LENGTH: 22 amino acids
( B ) TYPE: amino acid
( D ) TOPOLOGY: linear ( i i ) MOLECULE TYPE: protein ( v ) FRAGMENT TYPE: internal ( x i ) SEQUENCE DESCRIPTION: SEQ ID NO:3:

```
Val Leu Gly Gln Ala Thr Phe Tyr Asn Val Pro Ala Ala Leu Gly Gly
1               5                   10                  15
```

```
Val  Gly  Ala  Val  Ala  Gly
               20
```

CITRUS PROTEINS FOR USE IN FIELD DETECTION OF CITRUS BLIGHT USING IMMUNOLOGICAL TECHNIQUES

The application is a continuation, of application Ser. No. 07/792,558, filed Nov. 12, 1991.

BACKGROUND OF THE INVENTION

1. Field of the Invention

The present invention relates to purified and isolated citrus blight leaf proteins useful for the detection of citrus blight. In particular, the present invention relates to the purified and isolated citrus blight leaf proteins having a partially known amino acid sequence, antigens prepared using the citrus blight leaf proteins, antibodies prepared using the antigens and methods of diagnosis of citrus blight using electrophoresis and immunological techniques.

2. Description of the Art

Citrus blight is a citrus disorder of unknown etiology which causes significant citrus fruit and tree lose. The disease results in overall decline of plant vigor, ultimately leading to the need to remove affected trees and resulting in enormous subsequent economic loss.

Citrus blight is an extensive world-wide problem affecting numerous countries having large citrus industries, especially countries such as Argentina, Brazil, and South Africa, where citrus crops are an important part of the countries' economy. Blight has been known to exist in Florida for well over a century, where despite extensive research on the disease, investigators have failed to identify any causal agent. Citrus blight has been the most important cause of tree loss in Florida citrus orchards in recent years. The estimated annual loss to Florida citrus growers, including tree value and replacement cost, is about $52 million (Timmers, L., First Intl. Seminar on Citrus Rootstocks, San Pablo, Brazil, 1990).

The citrus blight syndrome begins as a delay or lack of new growth flush during the spring and a wilting of existing leaves. The wilting can not be corrected by irrigation. Subsequent seasonal growth exhibits increased leaf water potential, increased abscission of leaves, and death of terminal growing points. The metabolism of the tree is disrupted. Zinc, chlorides and sodium accumulate in the leaves. The enzymes, ribulose 1,5-biphosphate carboxylase and carbonic anhydrase, are also less active in blight stressed trees.

Recent studies have shown that the disorder might be transmitted by root grafting and therefor and infectious agent. In a study where seedlings were infected with *Xylella fastidiosa*, a xylem-limited, gram-negative bacterium, the seedlings developed some symptoms of blight. However, immature seedlings (<5 years) in the field are not susceptible to infection with the bacterium. Further studies failed to infect reconstituted trees, and citrus blight symptoms did not develop in trees grafted with buds, shoots, or roots from bacteria blighted trees.

In spite of the fact that citrus blight has no clear diagnostic visible symptoms, it has certain determinable characteristics which are used to distinguish it from other tree declines.

The leaves of affected trees exhibit zinc deficiency and zinc accumulates in other tissue, especially the trunks. The method of Wutscher, H. et al *Proc. Fla. State Hort. Soc.* 90:81–84 (1977) can be used to determine the zinc accumulation in trunk wood as a diagnostic for the disease. The method uses wood rather than bark since the percentage of increase in zinc concentration is much greater than with bark. However, since soils and applications of zinc as a fertilizer vary among orchards, it is essential to compare zinc levels in wood declining tree with those in healthy trees in the same orchard.

Absorption of water by the trunks of blighted trees was found to be abnormal and can be used in the diagnosis of the disease (See Cohen, M et al *Proc. Intl. Soc. Citriculture* 3:884–886 (1974)). Water flow in most limbs and small branches is comparable to that in healthy trees. However, water flow is impeded in the trunk and large roots and branches except for about the outer centimeter of xylem tissue. Smaller roots may be completely blocked or may show normal water flow. The water flow test for blight was refined and simplified by using a syringe to inject water into a small hole bored into the tree trunk (Lee, R. et al, *Plant Dis.* 68:511–513 (1984)). Healthy trees and those affected absorb from about 0.25 to 1.0 ml/sec whereas blighted trees absorb virtually no water.

Cytological research has revealed the presence of dark fibrous occlusions and amber, amorphous plugs in the vessels of blighted citrus trees. Amorphous plugs occurred more commonly and appeared to be more characteristic of blighted citrus trees. Brlansky, R. et al *Phytopathology* 74:1324–1328 (1974) demonstrated that restriction of water flow in blighted trees is most closely correlated to the numbers of amorphous plugs in the vessels and appears to be characteristic of blighted trees. However, caution must be used when identifying amorphous plugs because gum plugs formed in response to injuries or infections can appear very similar to amorphous plugs.

Imposition of stress on plants results in metabolic changes which can alter the types of proteins formed by cells. New proteins can also be induced in plants by the presence of pathogens. Derrick, K. et al (*Plant Dis.* 74:168–170 (1990)) looked for but did not find blight-specific proteins in either the leaves or bark of blight diseased trees. Derrick et al. did however report the presence in roots of a number of proteins that appear to be unique to blight. Derrick et al. failed to detect the blight-specific proteins in some stem samples and in root samples from two of 17 trees with symptoms. Derrick et al. inferred from this that the blight pathogen is unevenly distributed in infected trees.

The discovery and development of a sensitive and specific biological marker would allow diagnosticians and researchers to differentiate citrus blight from other physiological or pathological disorders and to detect the disease in asymptomatic trees. The ability to accurately diagnose citrus blight is crucial to preventing the enormous economic loss each year attributable to citrus blight. The present techniques for detecting citrus blight require determination of high zinc levels in bark or wood samples, impairment of water movement, and water deficits in leaves. These diagnostic techniques are destructive to young citrus trees due to necessity of repeated sampling and the increased incidence of pathogenic infection at the sampling sites. Furthermore, the current diagnostic techniques are expensive, time consuming and indirect techniques initiated after the blight has expressed itself in recognizable symptoms and well after the blight has started to seriously effect the tree's metabolism.

SUMMARY OF THE INVENTION

It is an object of the present invention to achieve a sensitive and specific diagnostic test for citrus blight that overcomes the problems encountered in the prior art.

The present invention relates to the discovery and use of novel proteins which were purified and isolated from citrus blight leaves and which are sensitive and specific indicators for the presence of citrus blight. The isolated and purified citrus blight leaf proteins have a molecular weight of about 10,000 to about 30,000 daltons.

The citrus blight leaf proteins of the present invention have been separated, purified and partially sequenced. One protein, SEQ ID NO. 1 has a partial amino acid sequence of: Gly Glu Gly Thr Ala Thr Phe Tyr Thr Pro Pro Tyr Val Pro Ser Ala. Another protein, SEQ ID NO. 2 has a partial amino acid sequence of: Val Asn Ala Val Ala Val Ileu Thr Gly Asn Asn Gly Arg Lys Gly Thr Val Ser Gly. A third protein, SEQ ID NO. 3 has a partial amino acid sequence of: Val Leu Gly Gln Ala Thr Phe Tyr Asn Val Pro Ala Ala Leu Gly Gly Val Gly Ala Val Ala Gly.

The purified and isolated citrus blight leaf proteins can be used to prepare antigens, which are in turn used to prepare antisera, from which specific antibodies to the citrus blight leaf proteins are obtained. Methods of diagnosing of citrus blight can then be run using electrophoresis and immunological techniques.

BRIEF DESCRIPTION OF THE DRAWINGS

FIG. 1. SDS-PAGE gel (4% stack, 18% resolving, 20×20 cm, 1 mm) Coomassie Brilliant Blue R-250 stained. Lane (1) Bio-Rad MW standards, 8 μg; (2) citrus blight Valencia leaf protein (no ultrafiltration), approximately 45 μg; (3) healthy soluble leaf protein (no ultrafiltration), approximately 50 μg; (4) citrus blight soluble leaf protein, 5 μg (ultrafiltered filtrate between $M_r$10,000–30,000 fraction); (5) healthy filtrate, 5 μg (ultrafiltered filtrate between $M_r$10,000–30,000 fraction); (6) ultrafiltrate $M_r$<10,000-blight filtrate; (7) ultrafiltrate $M_r$<10,000-healthy filtrate.

FIG. 2. Densitometry tracing of (A) citrus blight ultrafiltrates $M_r$10,000–30,000 fraction lane 4 (FIG. 1) and (B) healthy ultrafiltrate $M_r$10,000–30,000 fraction, lane 5 (FIG. 1).

FIG. 3. SDS-PAGE gel (4% stack, 18% resolving gel, 7×10 cm, 1 mm thick) silver stained. Lane (1) Bio-Rad MW standards, 1 μg; (2) Sigma myoglobin fraction standards, 1 μg; (3) citrus blight soluble leaf protein ultrafiltrate $M_r$10,000–30,000 fraction 2 μg; (4) healthy citrus leaf protein ultrafiltrate $M_r$10,000–30,000 fraction, 2 μg.

FIG. 4. Western blot of fractions obtained by ultrafiltration using antisera against the blight proteins. Lane (1) ultrafiltrate ($M_r$10,000–30,000 fraction) from citrus blight (5 μg); (2) ultrafiltrate from healthy Valencia leaf proteins (5 μg); (3) and (4) are $M_r$>30,000 excluded fractions of the respective samples in lanes (1) and (2). Visualization accomplished using horseradish peroxidase.

FIG. 5. A 12% SDS-PAGE Coomassie-Brilliant Blue-stained gel of different soluble protein sources from citrus leaves from stressed plants which were ultrafiltered and the $M_r$10,000–30,000 fraction run. Each lane has approximately 12.5 μg of protein, except for lane (8) which has 1.25 μg. Lane (1) tristeza virus-infected; (2) citrus blight (Valencia); (6) water stress (Valencia) (7) blank; (8) zinc deficient; and (9) $M_r$ standards (Bio-Rad).

FIG. 6. Western blot of the duplicate gel shown in FIG. 5. The antibody to citrus blight proteins was used at a 1:100 dilution visualized with peroxidase secondary antibody.

FIG. 7. Western blot of the $M_r$10,000–30,000 fraction (18% SDS-PAGE gel) probed with antibody produced by desorption from PVDF membranes. Lane (1) contains ultrafiltered $M_r$10,000–30,000 fraction probed with antibody produced from this fraction; (2) and (3) are the healthy and citrus blight $M_r$10,000–30,000 fractions, respectively, probed with desorbed antibody from upper band (arrow) and visualized with alkaline phosphatase: Lane (4) contains Coomassie Brilliant Blue-stained standards.

FIG. 8 Western blot of 18% polyacrylamide gel with leaf tissue of (lanes 1–4 and 8) healthy and (lanes 5–7) blighted Valencia orange trees; lane 9 are standards stained with Coomassie Blue R-250.

FIG. 9 Blot patterns for leaf extracts from (lane 1) Valencia orange tree protein sources and Bio-Rad low molecular weight standards, (lanes 2 and 3) healthy trees, and (lanes 4–7) blighted trees probed with antiblight IgG. Lane 8 is Bio-Rad low molecular weight standards stained with Coomassie Blue R-250.

FIG. 10 Western blot extracts from diseased and healthy (lanes 1 and 2) Hamlin and (lanes 3 and 4) Valencia orange trees. Further extracts were precipitated from Hamlin with ammonium sulfate and from Valencia with acetone from buffer extracts containing protease inhibitors. Lane 5 is leaf extract transferred to a PVDF membrane without further treatment and stained with Coomassie Blue R-250.

FIG. 11 Western blot of an 18% acrylamide gel with alkaline phosphatase visualization. Lane 1 is a positive Valencia blight control, lane 2–4 healthy Hamlin, and lanes 5–8 positive blight examples. Each lane contains 15 μl of a 6.2% suspension of the freeze-dried protein extract, except lane 9 which are BioRad LMW standards.

FIG. 12 Western blot of a number of different diseases and their reaction to the antibody to citrus blight leaf protein (CBLP). Lane 1-LMW biotinylated standards, 2-foot rot Phytophtora, 3-healthy, 4-psorosis, 5-psorosis, 6-healthy, 7-blight, 8-blight, 9-blight control, 10-healthy control. Lane conditions are the same as FIG. 11.

FIG. 13 Western blot of an 18% acrylamide gel. Lane 1-positive blight control, 2-healthy control, 3-Pierce's disease (PD) in grape, 4-healthy grape, 5-PD inoculated citrus, 6-PD inoculated citrus, 7 and 8-healthy trees from PD inoculation site, 9-LMW Coomassie blue stained standards (1 μg protein).

DETAILED DESCRIPTION OF THE INVENTION

In the present invention novel proteins, isolated and purified from citrus blight leaves, have been discovered which prove to be sensitive and specific indicators for the presence of citrus blight. Although not wishing to be bound by theory, it is possible these proteins may hold a link to a pathogen as the blight protein source; they could be either host-encoded or pathogen-encoded. Or in the alternative, the proteins may arise de novo from the host plant as a result of an unknown stress.

Using a non-denaturing extraction technique coupled with ultrafiltration, a 10–30 kDa fraction is isolated on sodium dodecyl sulfate-polyacrylamide gel electrophoresis (SDS-PAGE). Two distinct and adjacent bands, unique to blight, are separated at a molecular weight ($M_r$) of from about 12,500 to 13,000. These bands are made visible when stained with Coomassie Brilliant Blue or silver stain, but are negative to glycoprotein stains. These bands can be further separated into three proteins which have been assigned the names SEQ ID NO. 1, SEQ ID NO. 2, and SEQ ID NO. 3. The amino acid sequences for the proteins SEQ ID NO. 1, SEQ ID NO. 2 and SEQ ID NO. 3 have been partially determined.

Antibodies prepared against the citrus blight leaf proteins, isolated by preparative electrophoresis, react only with the citrus blight leaf protein fractions and are non-reactive to healthy leaf protein fractions. The antibodies are specific and sensitive to citrus blight leaf proteins and thus can be used to diagnose the onset of citrus blight prior to any visible tree symptoms.

The Western Blot separation technique coupled with the immunological techniques, form a test which when used to determine the presence of citrus blight leaf proteins proves to be extremely specific in distinguishing, healthy trees from citrus blight trees, but also citrus blight trees from trees afflicted with diseases other than citrus blight. In all the trees sampled using the combined test, regardless of scion or rootstock, the combined electrophoresis separation and antibody test correctly diagnosed citrus blight. The results correlated 100% with the zinc and water analysis citrus blight tests. The use of this leaf sampling test is a fast and nondestructive and provides the advantage of repeated sampling without injury to young trees.

Eighty-six sweet orange trees from three Florida grove locations were diagnosed as being healthy or blighted using the combined western blot and antibody test, using proteins extracted from citrus leaves. Extracted proteins were separated on 18% SDS-PAGE gels, electro-blotted onto a polyvinylidenedifluoride membrane, and probed with citrus blight antisera. This combined blot and antibody system was as reliable as conventional diagnostic system and in several cases detected the presence of blight before increased tissue concentrations of zinc, decreased water uptake, and wilt were observed. Results were the same for samples taken during winter dormant periods and samples taken during spring growth. The use of leaf samples for the diagnosis of citrus blight has the advantage of allowing repeated sampling, unlike xylem zinc analysis and water injection techniques.

No cross-reaction was found between the blight leaf protein antisera and extracts from citrus or grapes which had been inoculated with *X. fastidiosa*. The proteins appear resistant to protease activity, since extracting with or without a protease inhibitor cocktail and long dialysis times do not affect the results. The Western blot system for the diagnosis of citrus blight is highly specific and uses easily acquired leaf tissue in small samples. It also holds more promise as an earlier diagnostic procedure than either zinc or water injections. Additionally, trees of all ages may be sampled as long as leaf tissue is available, which is a distinct advantage to currently employed diagnostic methods.

To determine if the citrus blight marker proteins had any relationship to a common citrus pathogen, citrus tristeza virus (CTV) protein samples that contained the citrus blight marker proteins were reacted against eight monoclonal and polyclonal antibody sources made to coat protein using enzyme linked immunosorbent assay (ELISA). No positive reaction was found. Further, a polyclonal antibody to the pathogenesis-related protein (PR 1a, supplied by Y. Ohashi) had no reaction using a Western blot system (See Ohashi, Y. Plant Cell Physiol. 28:1227–1235 (1987)).

The citrus blight proteins have also been isolated under a number of environmental conditions during different growth cycles and resting stages with no difference found in the type of proteins visualized. This is evidence of the constant presence of these proteins once they are detected in the leaves of the affected trees. The blight proteins are found in both the Valencia and Hamlin orange varieties, which are the major varieties in Florida.

The use of electrophoretic techniques coupled with the ability to use the antibody test prove to be extremely effective in the earlier diagnosis of citrus blight. It offers another advantage over other diagnostic systems in that the test is nondestructive to the plant and thus can be used on young trees, and easily repeated if necessary.

Purification and Isolation of Citrus Blight Leaf Proteins

Leaves of citrus trees to be tested are collected and their source carefully noted. The freshly collected leaves are dipped in a 1% sodium hypochlorite solution, rinsed and blotted dry. The leaves are deribbed, plunged into liquid nitrogen and ground to a powder.

The leaves are placed in an extraction buffer forming a slurry. The buffer can be either a 8.4 or 7.0 buffer depending on the method of extraction to be used. The leaf proteins can be separated using either an ammonium sulfate precipitation method or an acetone precipitation method. The acetone precipitation method can be run with or without protease inhibitors. The resulting slurry is chilled and stirred.

If the ammonium sulfate precipitation method is used, the 8.4 pH buffered slurry is filtered, centrifuged and the pellet discarded. Ammonium sulfate is then added to the supernatant. The resulting precipitate is separated, dissolved in water, dialyzed, freeze dried and stored under a vacuum.

If the acetone precipitation is used, the 7.0 pH buffered slurry is centrifuged, the pellet is collected and re-extracted in buffer. The buffer optionally contains protease inhibitors. The combined slurry is centrifuged, the pellet discarded and the supernatant is filtered. Cold acetone is added to the supernatant resulting in precipitation. The precipitant is separated, dissolved in water, freeze dried and stored for further analysis.

The use of ultrafiltration to separate the 10,000 to 30,000 fraction of leaf proteins is especially useful in eliminating the problem of protein dissociation and interference from other low weight molecules. However, any extraction technique that sufficiently isolates the citrus blight leaf proteins from other proteins can be used and is within the scope of the present invention.

Western Blot Staining Technique

The leaf extract is separated using electrophoresis (SDS-PAGE) and stained using either Coomassie Blue or a silver stain. Molecular weight standards and samples known to contain citrus blight should be run with the samples to be tested. The formation of distinctive bands at about 12,500 to 13,000 is indicative of the presence of citrus blight.

The western blot staining technique can be used alone, to identify the presence of citrus blight leaf proteins in samples, however it is preferable to use the technique in conjunction with a confirmation technique such as labeled antibody binding. Separation and Partial Sequencing of the Citrus Blight Leaf Proteins SEQ ID NO. 1, SEQ ID NO. 2 SEQ ID NO. 3.

The some of the citrus blight leaf proteins of the present invention have been separated using iso-electric focusing, purified and partially sequenced. One protein, SEQ ID NO. 1 has a partial amino acid sequence of: Gly Glu Gly Thr Ala Thr Phe Tyr Thr Pro Pro Tyr Val Pro Ser Ala. Another protein, SEQ ID NO. 2 has a partial amino acid sequence of: Val Asn Ala Val Ala Val Ileu Thr Gly Asn Asn Gly Arg Lys Gly Thr Val Ser Gly. A third protein, SEQ ID NO. 3 has a partial amino acid sequence of: Val Leu Gly Gln Ala Thr Phe Tyr Asn Val Pro Ala Ala Leu Gly Gly Val Gly Ala Val Ala Gly.

Citrus Blight Leaf Protein Antigen Preparation

Citrus blight leaf antigen is prepared from citrus blight leaf protein extracts, which are prepared by either the ammonium sulfate or the acetone precipitation method. The sample is rehydrated, centrifuged and the supernatant is cleaned up using filters, electrophoresis, electro-elution, extraction methods or a combination. The antigen preparation is purified to preferably about 95% protein.

Citrus Blight Leaf Antisera Preparation

Antisera is prepared using the partially purified antigen preparation. The antigen preparation is administered to a mammal, preferably a rabbit. Blood is collected, the serum is separated and the IgG antibodies removed, preferably using either agarose-bound Protein A or Protein G.

Preparation of Monospecific Antibodies

In order to determine if the two proteins used as the antigens differ antigenically, a desorption technique was used to differentially bind the antibody IgG fraction. Antibodies of mixed specificity are bound to individual proteins that are separated by electrophoresis. The proteins were blotted and antibodies were used to probe the proteins, and then were desorbed by breaking the gamma chain bonds using pH change. The position of the blight CB1a and CB-1b (FIG. 1) proteins was determined by using PVDF membranes to transfer the initial protein fractions, and Coomassie staining the end lanes ensured the position. The initial binding and desorption of the proteins yielded antibodies which would bind differentially to one protein band using $BL_{IgG}$.

Confirmation of Antibody Specificity

The antibody produced in the antisera of rabbits was tested for specificity against various protein fractions and found to be specific for the fraction containing the citrus blight leaf proteins.

Diagnosis of Citrus Blight Using Electrophoresis and Immunological Techniques

The citrus blight leaf proteins can be extracted from leaves, placed on a SDS-PAGE and separated. The proteins can be identified using stains, or in the alternative, the proteins can be identified using immunological techniques. For example, the gel can be contacted with antibodies specific for the indicator proteins (CBLP). These antibodies can form a complex with the proteins and the complex identified.

Another method of identifying the presence of the citrus blight leaf proteins separated on SDS-PAGE, is to bind the antibody-antigen complex with and labeled anti-IgG antibody. By testing for the presence of the label one indirectly measures for the presence of the indicator proteins (CBLP).

The present invention is not limited any specific separation or identification methodology. Rather, all modifications obvious to one skilled in the art are envisioned and encompassed by the present invention. The following examples are offered to illustrate the present invention and are not intended to limit the scope of the invention.

EXAMPLE I

Purified and Isolated Citrus Blight Leaf Proteins

Leaves of healthy and citrus blighted Valencia and Hamlin sweet orange (*Citrus sinensis* L. Osbeck) cultivars were obtained from different Florida field sites and from greenhouse-potted and screenhouse-potted trees. All trees were grafted to rough lemon rootstock (*Citrus limon* L. Burm. f.) or sour orange (*Citrus aurantium* L.). All lamellar tissues were prepared according to the protocol of Raff, J. et al *Planta* 153:115–124 (1981) with slight modifications. Freshly collected leaves were dipped in a 1% sodium hypochlorite solution for 5 minutes and rinsed three times with tap water before the leaves were moved to the laboratory. The leaves were then rinsed with deionized water (Milli Q, Millipore, Bedford, Mass.) and blotted dry. Using powder-free vinyl gloves, the leaves were deribbed by tearing the lamellar tissue from the midvein, immediately plunged into liquid nitrogen and ground into a powder using a mortar and pestle. The ground leaves were then placed in an extraction buffer, containing 50 μm Tris, 1 mM $CaCl_2$, 1% insoluble polyvinylpyrrolidone (PVP) and 0.15M NaCl, pH 8.4, at 4° C. at a rate of 1 mL/g fresh weight of tissue. The slurry was stirred at 4° C. for 10 minutes and filtered through Miracloth. The filtrate was centrifuged for at least 10 minutes at 20,000 g and the pellet discarded. The supernatant fraction was brought to 85% saturated solution in ammonium sulfate and stirred for 18 hours at 4° C. The resulting precipitate was sedimented by centrifugation for 20 minutes at 20,000 g. The supernatant was discarded and the pellet was re-suspended in 20 × volume of cold water (4° C.). The re-suspended pellet was then dialyzed against 10 changes of cold deionized water, 4° C., using a 25 mm wide dialysis membrane with an $M_r$ 6,000–8,000 cutoff (Spectrapor, Spectrum Medical Industries, Los Angeles). The dialyzed preparation was then freeze-dried and stored in sealed glass containers under vacuum at −20° C.

A discontinuous sodium dodecyl sulfate-polyacrylamide gel electrophoresis (SDS-PAGE) system was used according to Laemmli, U.(*Nature* 227:680–685 (1970)), using either 12 or 18% acrylamide (See individual Figures), with a Mini Gel apparatus, 7×10 cm or Protean II, 20×20 cm (Bio-Rad, Richmond, Calif.) (See FIGS.). The protein-tracking buffer consisted of 4% SDS w/v, 5% 2-mercaptoethanol, 20% glycerol and 0.01% Bromophenol Blue in 62.5 mM Tris at pH 6.8. For each individual SDS-PAGE running condition, refer to the Figures. The SDS-PAGE gels were stained either with Coomassie Brilliant Blue R-250 or silver stain (Bio-Rad) (See Gultekin, H. et al., *Anal. Biochem.* 172:320–329 (1988) and Switzer, R. et al. *Anal. Biochem.* 98:231–237 (1979)).

The proteins separated by ultrafiltration are shown in FIG. 1. Lanes 2 and 3 show the blight and healthy protein extracts, respectively, without any ultrafiltration. Separation on a 4% stack and 12% resolving gel shows a pattern which has at least three proteins which are found in the $M_r10,000–30,000$ fraction region (lane 4). This area is below the $M_r14,400$ lysozyme marker. The healthy ultrafiltrate of the same type had only one major component which is found near the frontal region of the gel (lane 5), but does not coincide with the major protein bands from the citrus blight leaves. This gel also shows the efficiency of ultrafiltration as no bands appear in the $M_r>30,000$ range.

Figure 2A:
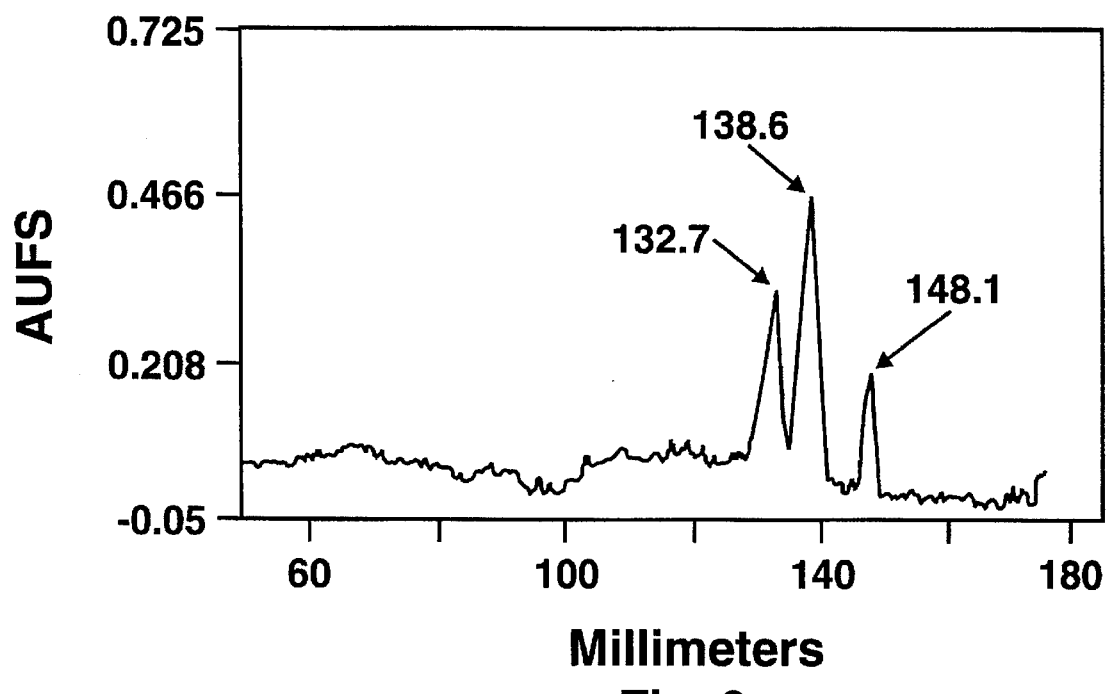
Figure 2B:
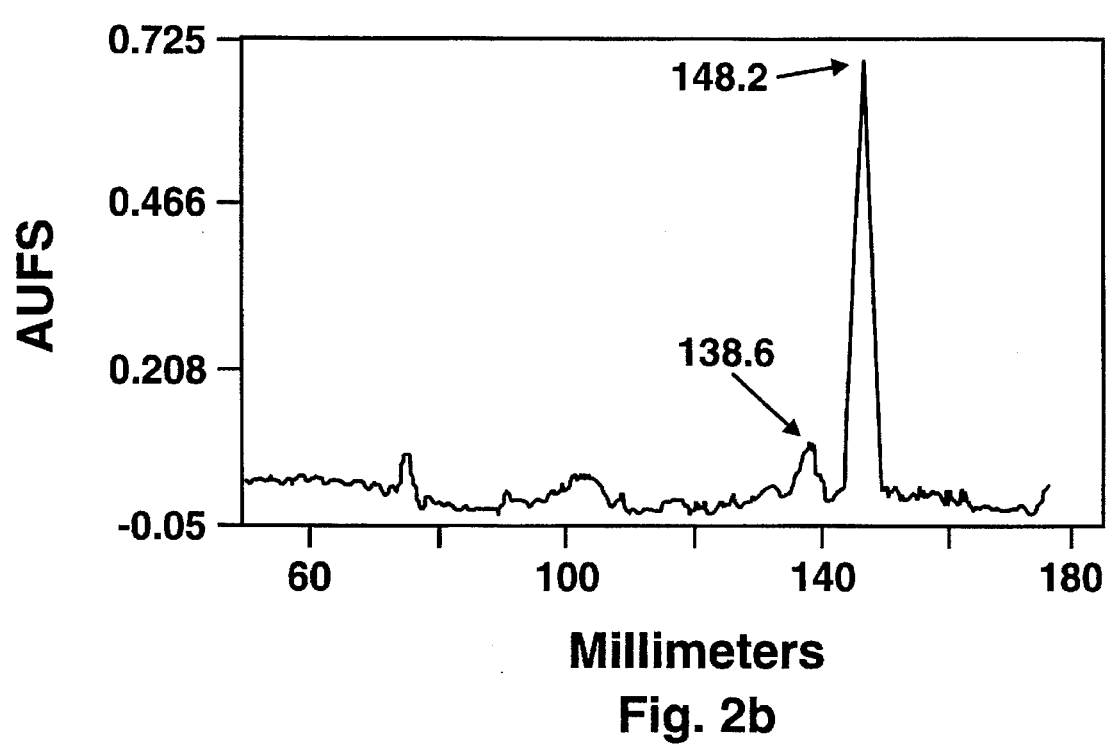
Figure 3:
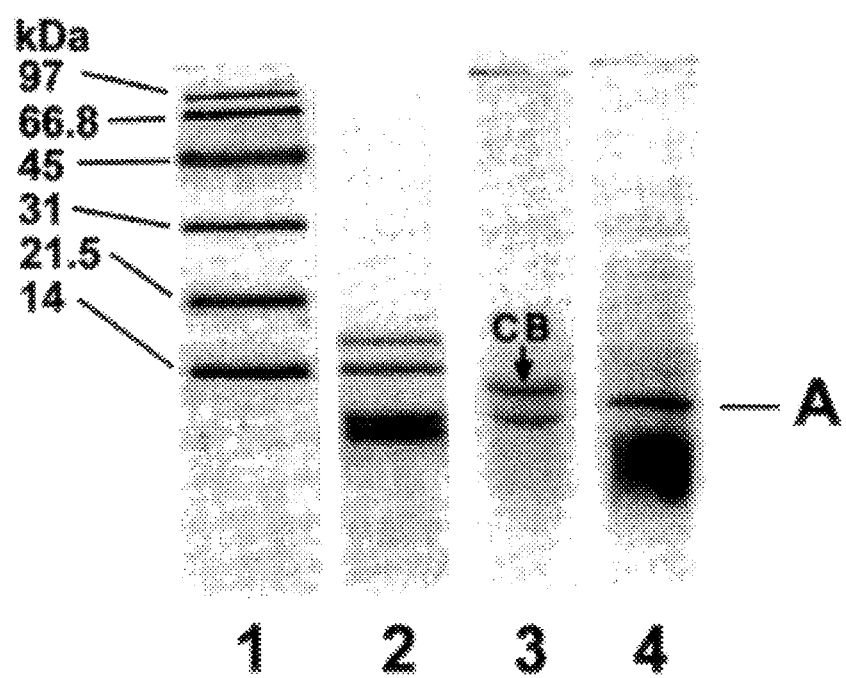

Using densitometry (FIG. 2) the mobility of the bands (in FIG. 1) clearly show that the proteins identified as CB-1a and CB-1b are unique to the citrus blight sample (132.7 mm). This particular region stains with much greater intensity in the blight sample than in the healthy sample. The opposite is true of the band with a mobility of 148.2 for blight and 148.1 (band B) for healthy, with the healthy sample having the greater intensity. As expected, no staining bands were found in the samples below the $M_r10,000$ cutoff, since an $M_r6000–8000$ cutoff dialysis tube was used in the initial extraction. The last centrifugation step ($M_r$ 10,000 cutoff) was used to concentrate the protein samples for further analysis. Further determination of the molecular weight of the proteins in lanes 4 and 5 is shown in FIG. 3, which shows the blight proteins CB-1a and CB-1b to have a molecular weight between $M_r12,500–13,000$, using a 4% stacking and 18% acrylamide resolving gel with the molecular weight standards: myoglobin ($M_r16,950$), myoglobin fragment I+II ($M_r14,400$), myoglobin fragment I ($M_r8,160$), and myoglobin fragment II ($M_r6,210$).

EXAMPLE II

Citrus Blight Leaf Protein Antigen Preparation

Antigens were prepared from 120 mg of prepared sample of freeze-dried crude protein from leaf extract (prepared as described in Example I), obtained from citrus blighted Valencia trees from Dundee, Fla. The protein sample was rehydrated with 8 mL of $H_2O$, vortexed for 2 minutes and centrifuged at 13,000 g for 10 minutes. The resulting supernatant was then loaded onto a $M_r$30,000 cutoff protein exclusion filter membranes (Unisep, Bio-Rad, Richmond, Calif.) which had been pre-run with $H_2O$ to remove preservatives. After volume stabilization at 3,000 g, the resulting filtrate was placed on an $M_r$10,000 cutoff filter. The retained concentrate ($M_r$10,000–30,000 fraction) was used for SDS-PAGE in a 12% polyacrylamide gel. Following electrophoresis, the portion of the gel containing the area of interest was excised, (approximately $M_r$13,000), and transferred to an electro-eluter (Bio-Rad) equipped with $M_r$ 3500 cutoff dialysis membrane in 25 mM Tris base, 192 mM glycine, 0.1% SDS, pH 8.25. Elution proceeded at 10 mA for 3 hours in the cold room (4° C.). The eluted material was then placed on an affinity column (Extraction Gel-D, Pierce Chemical, Rockford, Ill.) to remove residual detergents (0.8×4 cm polyethylene column with a 2 mL bed volume) (See Elzinga, M. et al. *Proc. Nat. Acad. Sci. USA* 81:6599–6602 (1984)). Gel material was equilibrated with $H_2O$ before the addition of the sample containing SDS. The SDS-free material was dialyzed against $H_2O$ to remove Tris and freeze-dried until used. The yield was 3.76 mg of dried material with 95% protein (Bio-Rad micro protein determination, bovine serum albumin standard) (See Bradford, M. *Anal. Biochem.* 72:248 (1976)).

EXAMPLE III

Citrus Blight Leaf Antisera Preparation

Antisera were produced in 4-month-old male out-bred rabbits which were injected with 1 mg of the freeze-dried, the 10,000 to 30,000 molecular weight partially purified antigen (prepared according to Example II) in 1 mL of phosphate buffered saline (PBS), containing monophospholipid A (250 µg/m), trehalose dimycolate (250 µg/m), cell wall skeleton of mycobacteria (230–250 µg/m), squalene (20 µ) and Tween 80 (0.2%) in sterile PBS for each injection (See Ribi, E. et al. *Rev. Infect. Dis.* 6:567–572 (1984)). The solution was administered intramuscularly with an injection schedule of 14 days between first and second injections. Blood was collected 10 days after the second injection by bleeding the peripheral ear vein (See Nerenberg, S. et al J. *Immunol. Methods* 24:19–24 (1978)). The collected blood was then spun at 1500 g to remove the red blood cells. The resulting serum was stored at −20° C. IgG was recovered from sera by agarose-bound recombinant Protein A following the supplier's protocol (See also Bigbee, W. et al. *J. Immunol. Methods* 55:277–296 (1982)).

EXAMPLE IV

Preparation of Monospecific Antibodies

Proteins concentrated by ultrafiltration between 10,000 and 30,000 molecular weight were separated by SDS gels and prepared as antigens in Example II. The proteins were transferred using Western blots produced by a Nova Blot (KB) to polyvinylidene difluoride (PVDF, Immobilon (a registered trademark), Millipore, Bedford, Mass.) membranes with 0.45 µm pore size which is a semidry system (See Towbin, H. et al *Proc. Nat. Acad. Sci. USA* 76:4350–4354 (1979) and Matsudaira, P. *J. Biolog. Chem.* 21:10035–38 (1987)). Blot conditions were 0.8 mA/cm² for 25 minutes with a buffer system consisting of 39 mM glycine, 49 mM Tris 0.0375% w/v SDS and 20% methanol. Blot purification of antibodies was performed using a modified technique described by Olmstead, J. in *Methods Enzymol.* 134:467–472 (1986) and Smith, D. et al in *J. Cell Biol.* 99:20–28 (1984). After the proteins were transferred from 1 mm thick gels to PVDF, both outside lanes were stained with Coomassie Brilliant Blue to determine the position of the bands. The rest of the membrane was then blocked with 3% gelatin in PBS. The blocked membrane was matched to the previously cut and stained lane (the proper orientation was maintained with pinholes or cutting corners) to visualize the position of the bands. Two bands were cut from the PVDF using individual templates made by staining two lanes with Coomassie Brilliant Blue. The PVDF strips were incubated individually in blight antibody ($BL_{IgG}$) solution for 3 hours in a heat-sealed bag (Dazy Corporation, Industrial Airport, Kans.) and rotated end-over-end at room temperature (25° C.). The strips were removed from the primary blight antibody ($BL_{IgG}$) and washed immediately with PBS, and then placed in 1.5 m centrifuge tubes. The bound IgG was removed by placing in 1 mL eluant (0.2 m glycine-HCl pH 2.8, ±0.5M NaCl) for 2 minutes. Immediately after the glycine-HCl wash, the membrane was removed and washed in 1 mL PBS. The eluant was immediately neutralized with 0.1M NaOH to pH 7.4 and transferred to a centrifuge tube (Centricons, Amicon, Danver, Mass.) to concentrate the recovered antibody protein. The process of reprobing the PVDF was possible, provided the PVDF was washed immediately after elution with PBS to prevent the denaturing of the antigen bound to the PVDF. The eluted concentrated antibodies were used to probe blight and healthy antigens bound to PVDF membranes and visualized with goat anti-rabbit antibody-conjugated to alkaline phosphatase secondary antibody (Ab) to determine the antibody-binding reaction by staining.

Figure 7:
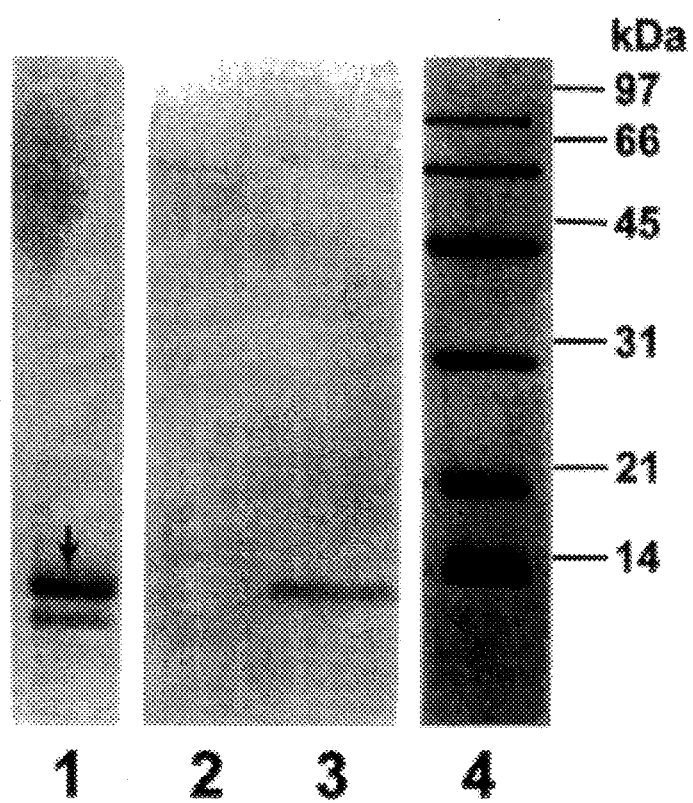
Figure 8:
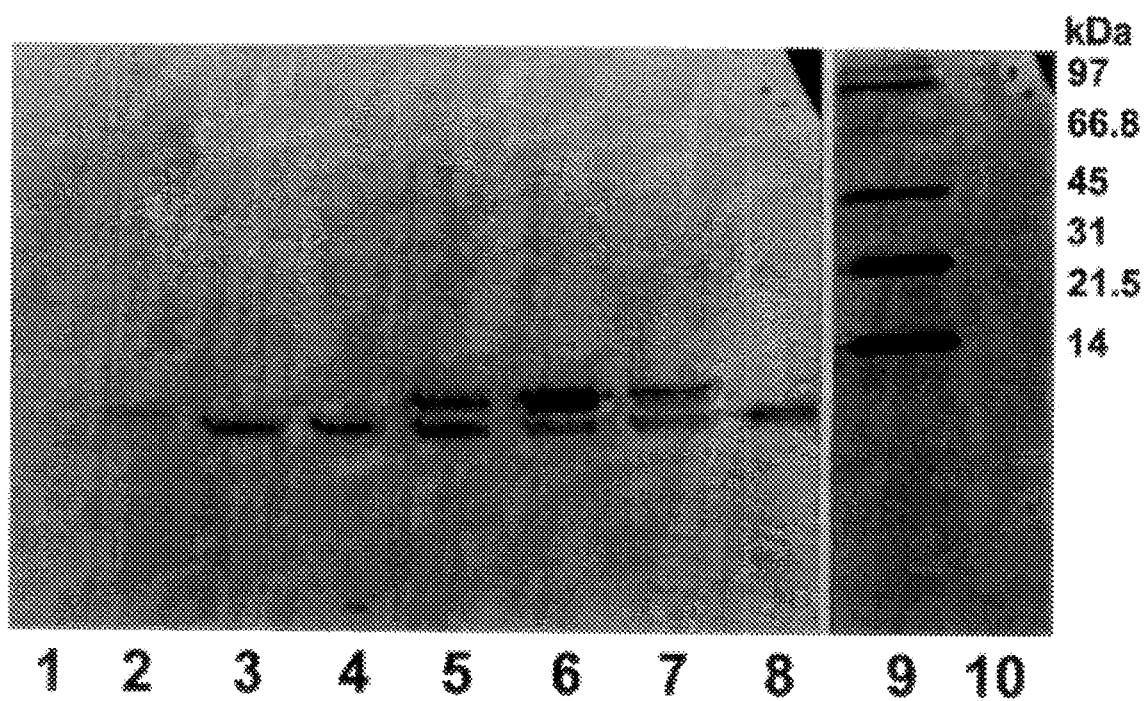
Figure 9:
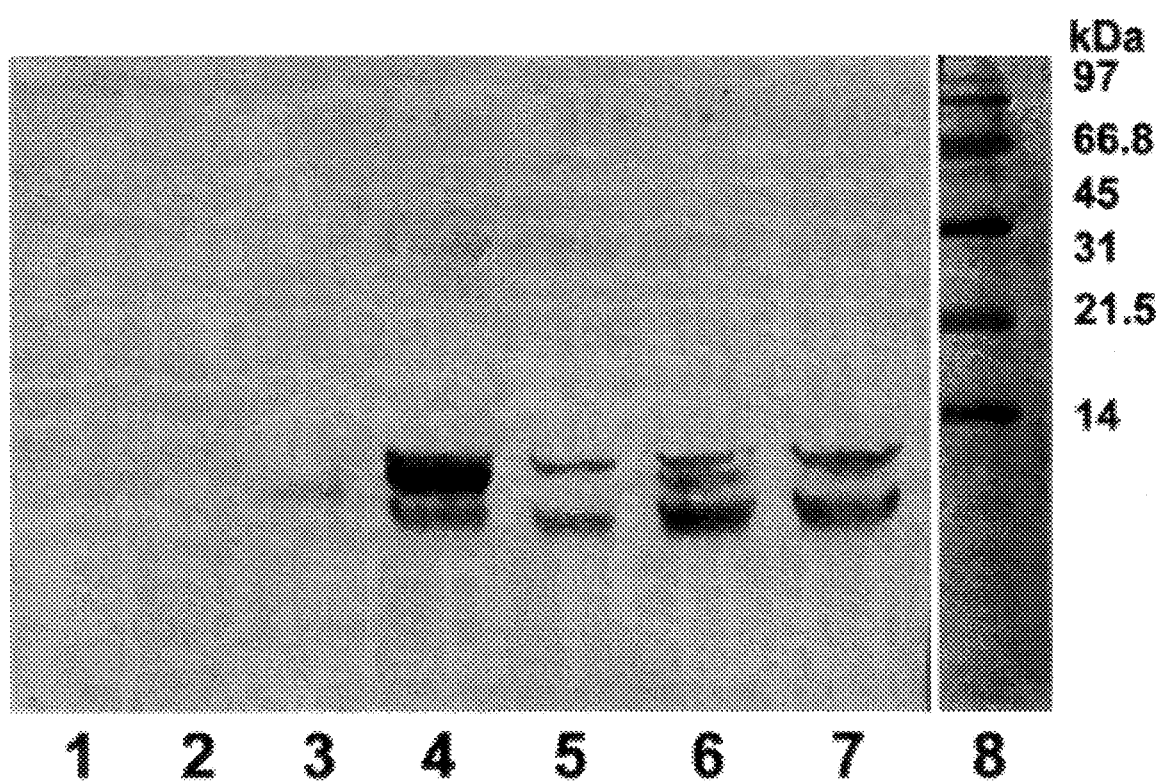

In FIG. 7, lane 3, there was a positive antibody-binding alkaline phosphatase reaction to only the citrus blight proteins to $BL_{IgG}$. The individual bands were then subjected to repeated incubations of 2 hours at 37° C. and the antibodies desorbed by a change in pH to 2.5 using a glycine buffer. The resulting collection of antibody protein was used to probe the healthy and blight proteins with the only positive reaction to the blight proteins (combined CB-1a and CB-1b, at arrow in figure). No reaction can be seen with the lower band, assumed to be band A, as in FIG. 1. No reaction was found with proteins from healthy leaf sources (lane 2). This experiment was repeated several times with the same results. The $M_r$13,000 did not exhibit positive results for either the Schiff base reagent or concanavalin A (Con A)-peroxidase assays for glycopeptides (See Clegg, J. Anal. Biochem 127:389–394 (1982)).

EXAMPLE V

Western Blot Staining and Immunological Techniques

Figure 6:
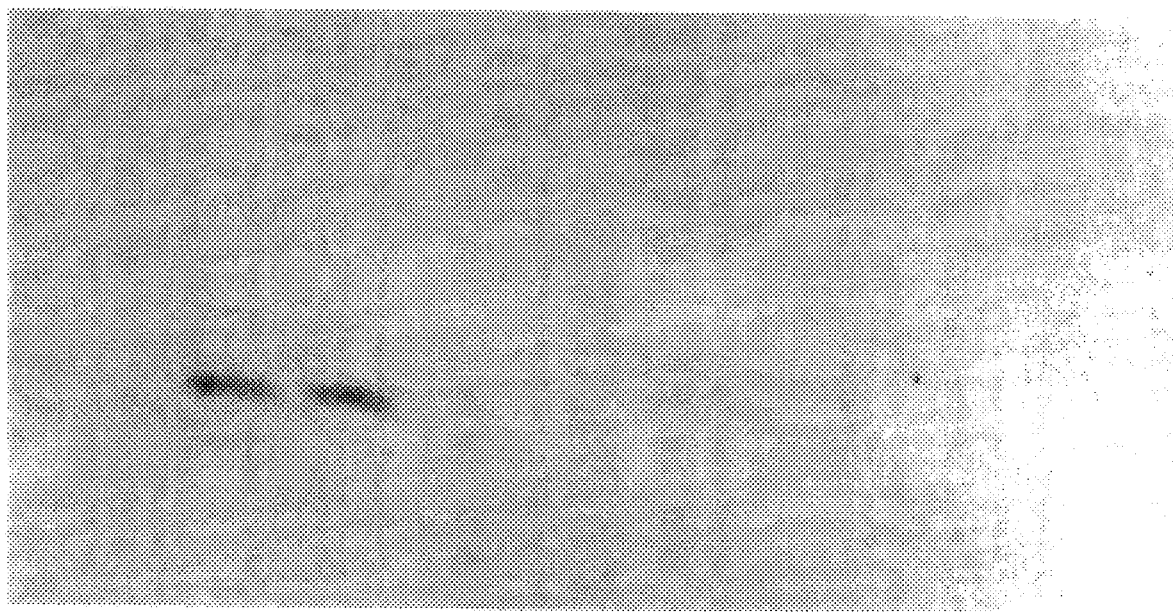

Proteins were transferred to PVDF membranes and placed in heat-sealed bags containing blocking solution (5% powdered milk, Carnation, plus 1% fish emulsion, (Nordland, New Brunswick, N.J.) in Tris-buffered saline (TBS) (See Saravis, C. *Electrophoresis* 5:54–55 (1984)) for 2 hours at 37° C. Alkaline phosphatase or horseradish peroxidase-conjugated goat-antirabbit IgG antibodies were used. For the alkaline phosphatase-conjugated IgG antibody the method of Blake, M et al described in *Anal. Biochem.* 136:175–179 (1984) was used with modifications. The prepared primary antibody, according to Example II, 1:100 dilution (in TBS with 1% powdered milk) was added to heat-sealed bags and incubated for a minimum of 2 hours or overnight. Peroxidase stains were carried out based on the periodate oxidation using a modification of the procedure of Wilson, M. et al Immunofluorescence and Related Staining Techniques, Elsevier North Holland Biomedical Press, Amsterdam, 1971, pp. 215–224. The membranes were blocked with 3% gelatin (Bio-Rad) in TBS for 3 hours or overnight in a heat-sealed bag, then washed three times with 5 mL TBS. The primary antibody to blight protein was diluted 1:100 in TBS with 1% gelatin and placed in a new bag. After incubation for 3 hours at room temperature with constant rotation, the PVDF membrane was washed three times with TBS and placed in a new bag. The blot was then incubated in a dilution of goat antirabbit horseradish peroxidase-labeled secondary antibody 1:1500. After 1 hour incubation and washing (three times with TBS for 5 min), the substrate (4-chloro-1-naphthol, 0.003% w/v in methanol, 0° C.) was added to $H_2O$ (0.015% w/v in TBS, 0° C.). The reaction was stopped with $H_2O$ after color development. The results are shown in FIGS. 4 and 6.

EXAMPLE VI

Confirmation of Antibody Specificity

Figure 4:
Figure 5:
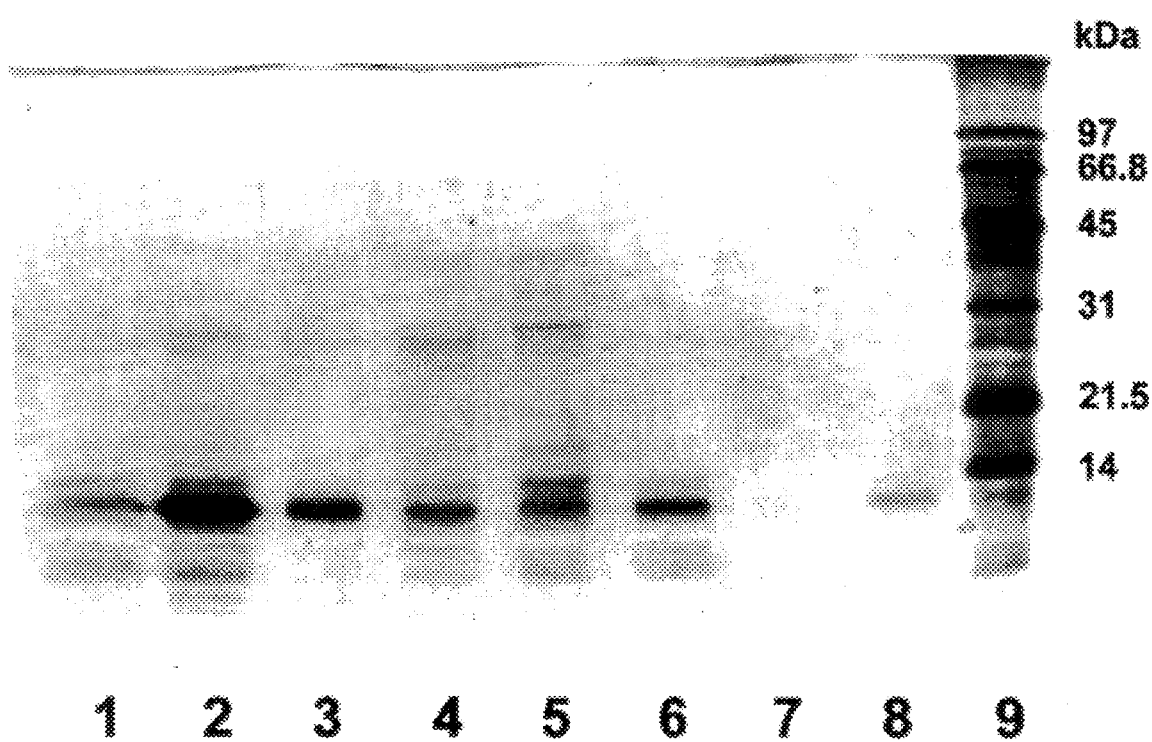
Figure 10:
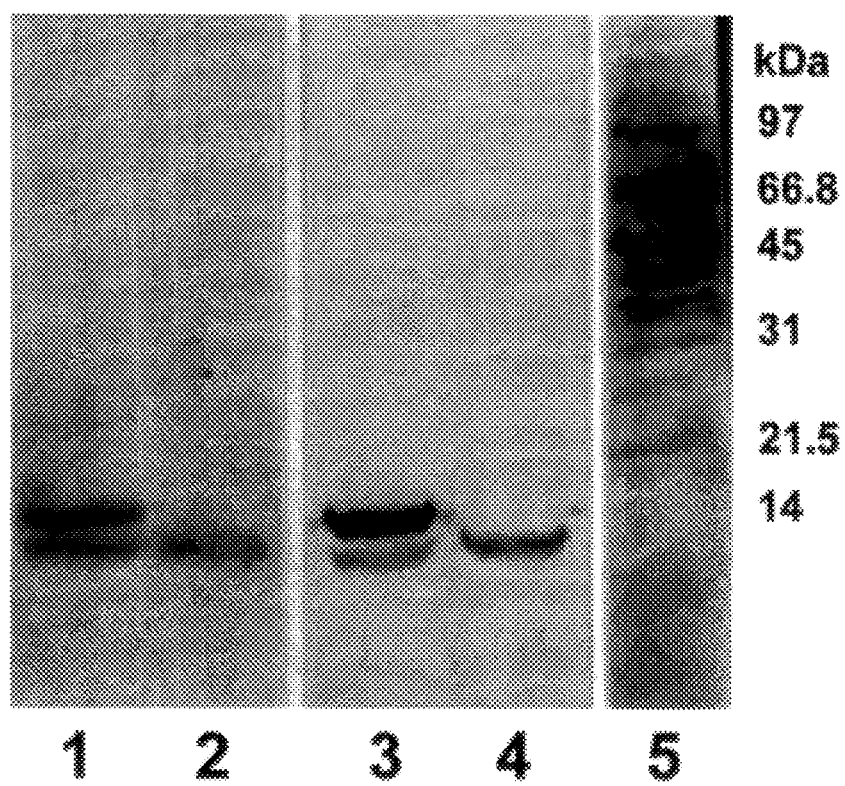

The unseparated antibody which was produced in rabbits to the $M_r12,500–13,000$ bands was incubated with the ultrafiltration fraction $M_r>30,000$ and the $M_r10,000–30,000$ fractions as well as the $M_r>10,000$ fractions, only the fraction containing the $M_r10,000–13,000$ protein was found cross-reactive with the antiblight sera (FIG. 4). The separation of the two bands is not complete as evidenced by the lower acrylamide percentage (12%) in FIG. 1. Band A of the healthy sample does not coincide with any band in the citrus blight sample using the higher acrylamide concentration (18%) of FIG. 3 and is probably the protein band A found in the 12% gel of FIG. 1.

EXAMPLE VII

Differential Diagnosis of Citrus Blight

To determine if these proteins were produced by other types of disease stresses, different stress source proteins, prepared identically with equal protein concentrations were compared (FIG. 5). Trees infected with CTV (lane 1), water stress to −2.5 mPa (lane 6) for 10 days and the presence of *Phytophthora parasitica* infection (lane 4), as well as severely Zn-deficient lamellar tissue, are represented (lane 8). All of the lanes contain proteins with molecular weights near 13,000. However, lanes 2 and 3 from two blighted sweet orange sources are characterized by an especially strong staining band. Similar protein bands are found in this area in lane 6, which contained an extract from a water-stressed sweet orange tree. Water stress is a symptom of blighted citrus trees, but only the lanes containing blight-source proteins developed positive antisera response with peroxidase-conjugated secondary antibody (FIG. 6). Although proteins were calculated, the different lanes—such as lane 8 did not stain well due to experimental error, probably due to errors in protein determination or interfering compounds in the individual samples. Nonspecific binding was tested using pre-immune serum from the same animals with negative responses.

EXAMPLE VIII

Separation and Partial Sequencing of the Citrus Blight Leaf Proteins CB1, CB2 and Cb3.

The two CB-1a and CB-1b protein bands were separated into three protein bands, named SEQ ID NO. 1, SEQ ID NO. 2 and SEQ ID NO. 3.

Citrus blight leaf proteins were extracted using the method of Example I. The citrus blight leaf proteins were loaded into a free zone iso-electric unit (Rotofor, Bio-Rad) at a rate of 1.5 mg of protein which was prepared by collecting a molecular weight cut off between 10,000 and 30,000 molecular weight (protein concentration determined by R-250 Coomassie using the Bradford method). In a total volume of 55 mL of a 1% ampholyte solution with a 3–10 pH range. The proteins were separated according to manufactures instructions until the mA reading on the power supply reached a plateau (approximately 3 hours). The protein fractions were then collected and the resulting solutions were dialyzed against distilled water. The protein fractions were then concentrated by lyophilization and separated using 20% SDS-PAGE gels and electro-transferred according to the conditions of the Examples above. The electro-transferred proteins were visualized on PVDF with R-250 Coomassie and the resulting bands were excised for micro-sequence analysis.

The three protein bands SEQ ID NO. 1, SEQ ID NO. 2 and SEQ ID NO. 3 were sequenced using a gas/liquid sequenator (Applied Bioscience) and according to the methods described by Matsudaira, P. *J. Biolog. Chem.* 21:10035–38 (1987) and the following partial sequences were obtained.

CB1
Gly Glu Gly Thr Ala Thr Phe Tyr Thr Pro Pro Tyr Val Pro Ser Ala
5 10 15

CB2
Val Asn Ala Val Ala Val Ileu Thr Gly Asn Asn Gly Arg Lys Gly Thr
5 10 15

Val Ser Gly
19

SEQ ID NO. 3
Val Leu Gly Gln Ala Thr Phe Tyr Asn Val Pro Ala Ala Leu Gly Gly Val
5 10 15

Gly Ala Val Ala Gly
20

These structures were checked for homology using three data bases available from the APAT (peptides sequences which have been patented), University of Wisconsin protein data base and the Swiss Protein Data base.

These sequences make it possible to make synthetic proteins homologous to the citrus blight proteins extracted from blighted leaves. These may in turn be used to generate specific oligonucleotides to be used as probes in diagnostic techniques and further isolate and characterize the nucleotide coding sequence.

EXAMPLE IX

CBLP Method of Diagnosing Citrus Blight

Samples (30-gm) of young, fully expanded leaves were harvested from sweet orange trees located in three areas of Florida: Fort Pierce during December and February, St. Cloud during December and April, and Davenport during July and August. The trees were either cv. Valencia or cv. Hamlin grafted to rough lemon (*C. limon* (L.) N. L. Burm.) or sour orange (*C. aurantium* L.) rootstock. Although the trees varied in age from 15 to 30 yr, most were 30 yr old. The harvested samples were washed in 1%(v/v) sodium hypochlorite (20% household bleach) for 5 min, rinsed in tap water, washed in deionized water, and blotted dry before extraction. Wearing powder-free vinyl gloves, tissues was removed from the midribs of the leaves. The tissue was immediately frozen and crushed in liquid nitrogen with a mortar and pestle. The ground leaves were placed in an extraction buffer (50 mM Tris, 1 mM $CaCl_2$, 1% [w/v] insoluble polyvinylpyrrolidone [PVP], 0.15M NaCl, pH 8.4, 4° C.), 10 ml/g fresh weight of tissue. The tissue slurry was stirred at 4° C. for 10 min and filtered through Miracloth. The liquid phase was centrifuged for at least 10 min at 20,000 and the pellet discarded. Ammonium sulfate was added to 85% (w/v). This mixture was stirred for 18 hour at 4° C. The resulting precipitate was sedimented by centrifugation for 20 minutes at 20,000 g. The pellet was dissolved in ×20 volume of water, and the solution was dialyzed against 10 changes of water using a 6,000- to 8,000- $M_r$ cutoff tubing (Spectrapor). The extract was freeze-dried and stored in sealed glass containers under vacuum at −20° C. Another method of extraction which can be used includes protease inhibitors and acetone precipitation (shown in Example XI)(Wilt, W. et al *Hort Science* 23:768–770 (1988)).

The SDS-PAGE (18% acrylamide) system of discontinuous electrophoresis according to Lammeli, U. (supra) was used with a Mini-Gel apparatus (Bio-Rad, Richmond, Calif.). The sample buffer consisted of 4% (w/v) SDS, 5% (v/v) 2-mercaptoethanol, 20% (v/v) glycerol, and 0.01% (w/v) bromophenol blue in 62.5 mM Tris, pH 6.8. Electrophoretic conditions were constant 200 V for 1 hr (4° C.). The SDS-PAGE gels were stained with either Coomassie Blue R-250 or Coomassie Silver (BioRad) according to the method of Switzer, R. et al, (supra). Reagents for electrophoresis and low molecular weight standards were from Bio-Rad.

Proteins less than 30,000$M_r$ were removed from the total soluble leaf extracts by ultra-filtration (30,000-$M_r$ cutoff filters) and electrophoresed. The bands just below the lysozyme standard (14,600$M_r$) were electro-eluted, and the SDS was removed, as described in Example II. The antigen (200 μg) was dissolved in 1 ml of sterile PBS adjuvant solution containing monophospholipid A (250 μg/ml), trehalose dimycolate (250 μg/ml), cell wall skeleton of mycobacteria 250 μg/ml), squalene (20 μl), and Tween 80 (0.2%), v/v. The solution was injected intramuscularly into 4-mo-old male rabbits at a 14-day interval, according to the methods of Ribi, E. et al. (supra). Blood was collected from the peripheral ear vein 10 days after the second injection, according to the methods of Nerenberg, S. et al (supra.). The clotted sera were spun at 1,500 g to remove the red blood cells, and the serum was stored at −20° C. IgG was removed from the serum by the use of agarose-bound recombinant protein A (Beckman, Fullerton, Calif.)(See Bigbee et al supra) and Langone, J. *J. Immunol. Methods* 55:277–296 (1982)) as per the manufacturer's protocol.

Proteins were transferred onto a polyvinylidenedifluoride (PVDF) (Immunoblon P, Millipore) transfer membrane by a semidry system (Nova blot)(See Towbin, H. et al supra). Blot conditions for the citrus blight antisera probing were 0.8 mA/cm$^2$ for 25 min with a buffer system consisting of 39 mM glycine, 48 mM Tris, 0.0375% (w/v) SDS, and 20% methanol. Slot blots stained with Coomassie Blue R-250 were used to determine the amount or protein delivered to each electrophoresis lane (See Bradford, M. *Anal. Biochem.* 72:248 (1976)). Stained protein content was measured with a Shimadzu CS9000 (Kyoto, Japan) scanning densitometer at 595 nm. Controls were derived from bovine serum albumin (Sigma Type V). After probing with citrus blight antisera was completed, blots were visualized by use of alkaline phosphatase conjugated goat antirabbit secondary antibody (Bio-Rad).

The use of PVDF membranes and alkaline phosphatase-conjugated antibodies greatly increased the sensitivity of this method over the use of nitrocellulose. Apparently, the PVDF membranes are hydrophobic longer during the transfer and blocking procedures than the nitrocellulose. The use of alkaline phosphatase provided greater sensitivity than would peroxidase-conjugated secondary antibodies, because of the increased color stability of the phosphatase. According to the manufacturer, alkaline phosphatase-conjugated materials have a 10-fold increase in sensitivity over peroxidase.

Two methods of diagnosis were used on healthy and blighted plants: 1) zinc analysis (See Cohen, M et al *Proc. Int. Soc. Citric* 3:884–886 (1974); Smith, P. *Proc. Fla. State Hortic. Soc.* 87:91–95 (1974); and Wutscher, H. *Proc. Fla. State Hortic. Soc.* 61:572–576 (1977)) and water uptake (See Lee, R. et al., *Plant Dis.* 68:511–513 (1984)) and 2) the western blot system.

The Western blots of extracts from blighted trees contained multiple protein bands (FIG. 8, lanes 5–7), whereas a single band or no positive reactions were observed for healthy trees (FIG. 8, lanes 1–4 and 8). Blight-associated proteins occurred below the molecular weight standard of 14,600 (lysozyme) (FIG. 8, lane 9). Thus, the $M_r$ of the blight proteins was about 13,000. The molecular weight standards used were 2 μg of protein per lane, whereas the unknown tree samples were 3.2 μg. The multiple banding pattern is suggestive of several compounds as antigens in blight (FIG. 9, lanes 4–7).

Extracts from diseased trees of both Valencia and Hamlin reacted to the antiblight IgG fraction of the sera (FIG. 10). Leaf proteins from Hamlin were precipitated by ammonium sulfate (FIG. 10, lanes 1 and 2) and leaf proteins from Valencia, by acetone containing protease inhibitors (FIG. 10, lanes 3 and 4). The banding patterns with both extracts were identical. Leaves from blight trees (FIG. 10, lanes 1 and 3) had multiple bands, and those from healthy trees (FIG. 10, lanes 2 and 4) had single bands.

Extracts of leaf samples from a typical double-banding pattern for the blight leaves and a single-banding pattern (or no band) for the healthy leaves were found in samples from all three grove locations. A sample from a blight-positive tree was electrophoresed, blotted, and cut from the original PVDF membrane and stained with Coomassie Blue R-250 (FIG. 10, lane 5). Clearly, a number of protein bands from leaf tissue extractions were visible in the Coomassie-stained blot that did not appear after antiblight probing, indicating specificity to the antibody.

The antisera reacted with the blight-associated proteins from the three grove locations tested. A third band was observed in the St. Cloud sample, suggesting that the upper band has more than one component.

For the 10 trees from Fort Pierce, the blight antiserum was positive for all trees diagnosed as having blight by method 1 and negative for all trees diagnosed as apparently health (See Table 1). Of the 19 trees sampled from St. Cloud, 10 were diagnosed as blighted by method 1 and 15 by method 2. None of the trees diagnosed as blighted by method 1 were rated blight-free in the antisera test. Subsequently, each of the trees diagnosed as blight-free by method 1 and blighted by method 2 developed the elevated zinc and water stress symptoms characteristic of citrus blight.

TABLE 1

Diagnosis of citrus blight at three locations in Florida

| Location | No. of Trees | Method 1 Blighted | Healthy | Method 2 Blighted | Healthy |
| --- | --- | --- | --- | --- | --- |
| Fort Pierce | 10 | 5 | 5 | 5 | 5 |
| St. Cloud | 19 | 10 | 9 | 15 | 4 |
| Davenport | | | | | |
| Site 1 | 37 | 24 | 13 | 25 | 12 |
| Site 2 | 20 | 11 | 9 | 13 | 7 |

Two groups of trees were tested at Davenport. In the first group (37 trees), 24 trees were diagnosed with blight by method 1 and 25 by method 2. The tree considered diseased by method 2 and healthy by method 1 was later found to be in the early states of blight. In the second group (20 trees), 11 trees were diagnosed as blighted by method 1 and 13 by method 2. Again, none of the trees diagnosed as blighted by method 1 were diagnosed as blight-free by method 2. No cross-reaction occurred with pre-immune rabbit sera or the alkaline phosphatase secondary antibody with the western blotted proteins from leaf sources.

EXAMPLE X

Confirmation of Diagnostic Differentiation-using CBLP Method of Diagnosing Citrus Blight The trees that were sampled consisted of cultivars of sweet orange and grapefruit from a number of field and greenhouse locations in the state of Florida and Beltsville, Md. All trees were between 2–40 years old and the 7 rootstocks were: rough lemon (*Citrus limon* (L.) Burm. f), macrophylla (*Citrus macrophylla* Wester), Carrizo citrange (*Citrus sinensis* (L.) Osbeck x *Poncirus trifoliata* (L.) Raf.), Cleopatra mandarin (*C. reticulata* Tan.), Rangpur lime (*C. reticulata* hyb.), Trifoliate orange (*Poncirus trifoliata* (L.) Raf.), and sour orange (*C. aurantium* L.), citron (*C. medica* L.), tangelo (*C. sinensis* L. Osbeck x *C. paridisi*). Scion cultivars include 'Homassasa,' 'Red Blood,' 'Red Sweet,' 'Pera,' 'Hamlin,' 'Valencia,' 'Navel,' 'Pineapple,' 'Temple' oranges, and 'Red blush,' 'Marsh,' and 'Duncan' grapefruit (Table 2).

All samples were double blind (Table 2). Samples were collected and coded by individuals other then those in the testing laboratory and their identity not revealed until the analysis was complete.

One gram samples of young, fully expanded leaves were collected from trees of various scion and rootstock combinations (St. Cloud, and Ft. Pierce). Rootstocks and scions are listed in Table 2. The samples were washed in 1% (v/v) sodium hypochlorite (20% household bleach) for 5 min, rinsed in tap water, washed in deionized water, and blotted dry before extraction. Laminae were detached from the midribs, powder-free vinyl gloves were used to minimize contamination when the plant tissue was handled, immediately frozen in liquid nitrogen and crushed with a mortar and pestle. The ground leaves were placed in 7 ml of 4-morpholinepropanesulfonic acid (Mops)/NaOH buffer/g tissue. The buffer contained 100 mM Mops/NaOH (pH 7.0), 1 mM dithiothreitol, 1 mM EDTA, 1% (w/v) insoluble polyvinyl pyrollidone (PVP), 1 mM phenylmethylsulfonyfluoride, 1 mg.liter$^{-1}$ leupeptin, and 0.5 mg.liter$^{-1}$ aprotinin, 0.5 mg.liter$^{-1}$ pepstatin. The slurry was agitated on ice for 10 min by occasional shaking. The undissolved material was pelleted by centrifugation at 3500× g for 10 min. The pellet was re-extracted in the same manner, and the filtrate was centrifuged for at least 10 min at 11,000 g and the pellet discarded. The supernatant was filtered through Whatman #1 paper. Cold (−20° C.) acetone was added to the supernatant (3× volume) and stored at −20° C. for 1 hr. The resulting precipitate was sedimented by centrifugation at 3,000 g for 20 min. The acetone-buffer centrifugate was discarded and the precipitate dissolved in 1 volume of water. This was then freeze dried and stored at −20° C. for further analysis (Witt, W. et al., *Hort. Sci.* 23:768–770 (1989)) and contained the presumed citrus blight-associated protein.

For electrophoresis—the SDS-PAGE (18% acrylamide) discontinuous system of Lammeli (supra) was used in a Mini-Gel apparatus (Bio-Rad$^R$, Richmond, Calif.). The gels were 1.0×80×73 mm in size. The sample buffer consisted of 4% SDS (w/v), 5% (v/v) 2-mercaptoethanol, 20% (v/v) glycerol and 0.01% (w/v) bromophenol blue in 62.5 mM Tris, pH 6.8. The samples were electrophoresed at constant 200 v for 1 hr (4C). The SDS-PAGE gels were stained with Coomassie Blue R-250 (Bradford, M. Supra). Reagents for electrophoresis and low molecular weight (LMW) standards were from Bio-Rad$^R$.

Antiserum to the blight-associated proteins was prepared according to a protocol of Example III. The IgG was removed from the serum by the use of agarose bound recombinant Protein G (Genex, Gaitherburg, Md.) (Fahnstock, S. et al., *J. Bacteriol.* 167:870–880 (1986)) as determined in the manufacturer's protocol.

For blotting, the proteins were transferred onto polyvinylidenedifluoride (PVDF) (Immobilon P$^R$, Millipore) transfer membrane (Gultekin, H. et al *Anal. Biochem.* 172:320–329 (1988)) using a Nova blot$^R$ (LKB) semi-dry system (Towbin, H. et al, supra). Blot conditions were 0.8 mA/cm$^2$ for 25 min with a buffer system consisting of 39 mM glycine, 48 mM Tris, 0.0375% w/v SDS and 20% methanol. Stained protein content was measured with a Shimadzu CS9000 scanning densitometer (Kyoto, Japan) at 595 nm with Coomassie Brilliant Blue staining. Controls were derived from Bovine Serum Albumin (Sigma Type V). Blots were visualized with alkaline phosphatase after probing with citrus blight antisera (Blake, M. et al., *Anal. Biochem.* 136:175–179 (1984)) goat anti-rabbit secondary antibody at a 1:3000 dilution in PBS containing 0.02% NaCN$_3$ (Bio-Rad, Richmond, Calif.).

Blight diagnosis was accomplished by zinc analysis (Cohen, 1974 supra; and Wutscher, 1977 supra) and water uptake in trunk injection (Lee, 1984 supra). Zinc analysis and water uptake analysis are Diagnosis A and the CBLP Western blotting technique is Diagnosis B.

All the samples tested are listed in Table 2. Diagnosis B (CBLP-antibody test) accurately diagnosed the presence of citrus blight in all locations, but was negative for all other citrus diseases. There was no positive response from trees with other diseases common in Florida, including tristeza, phytophthora, xyloporosis, psorosis, and exocortis all tested negative. Rio Grande Gummosis, a disorder with an unknown cause also tested negative. Trees diagnosed as positive by Diagnosis B also had high wood zinc (20 ppm) and low water uptake in syringe injection. All varieties and rootstock combinations diagnosed to have blight by Diagnosis A (zinc and water uptake) also tested positive by Diagnosis B. Diseases which affect leaf morphology (including likubin, South African Greening, Gummy Bark, and psorosis) tested negative by Diagnosis B. Water stress in the field (Table 2 samples 108 and 109) of Pineapple sweet orange and plants in greenhouse experiments (Table 2 samples 22,23,24) were also negative to Diagnosis B. Citrus nematode infested trees gave a weak reaction to the antibody in a region near, but not coincident with citrus blight leaf protein. No reaction to the antibody occurred in samples from citrus nematode infested greenhouse sources. The citrus nematode-infested Navel orange trees in the field showed no signs of stress, such as leaf wilting, during the sampling period.

Figure 11:
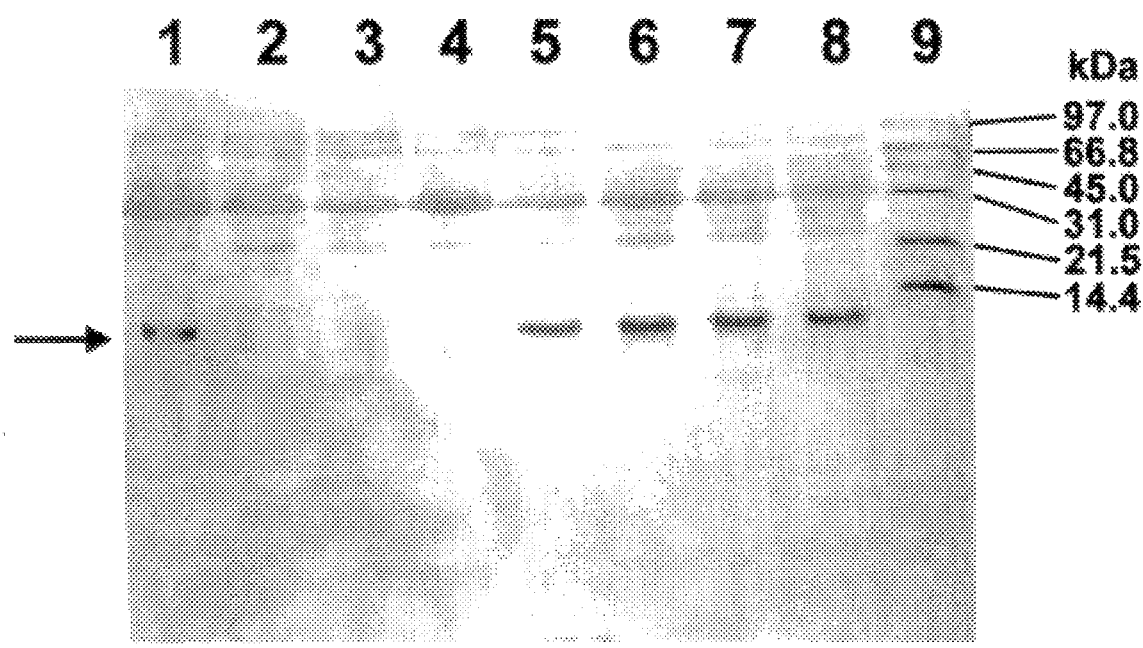
Figure 12:
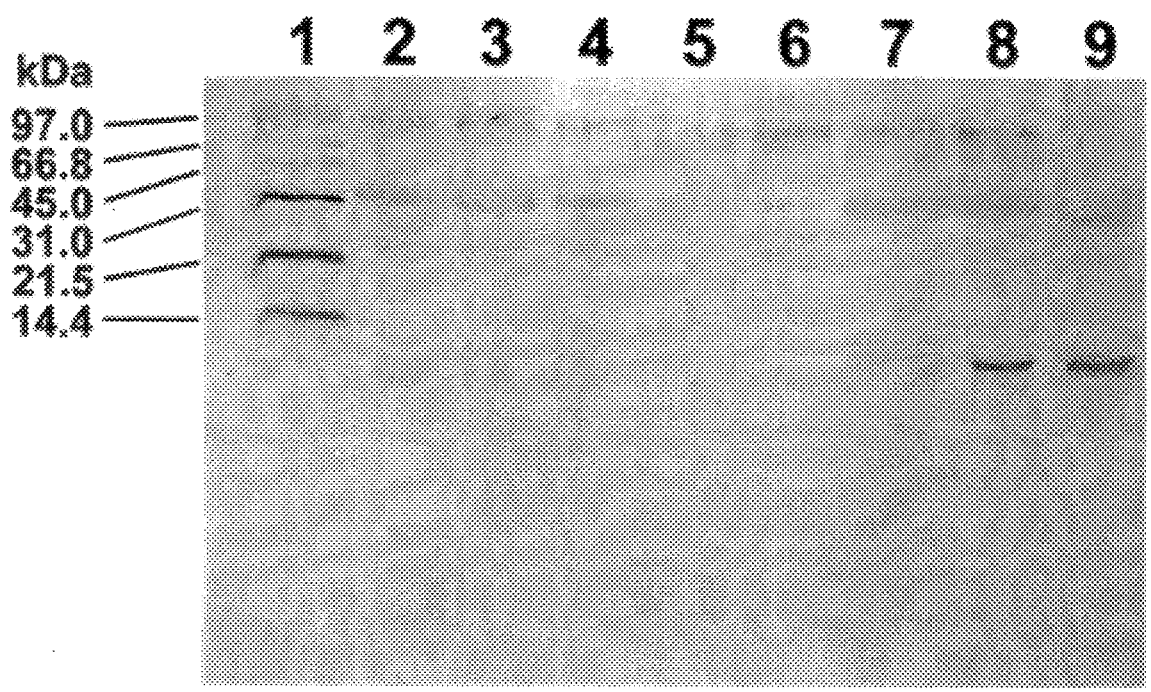

Examples of the western blot patterns obtained by Diagnosis B are shown in FIG. 11. Lane i is a sample from a positive control tree, showing the characteristic, positive band located below the 14 kDa standard (lane 9). Lanes 2, 3, and 4 have no positive bands below 14 kDa, corresponding to the positive blight control (arrow). Examples of positive antibody reactions to the blight-associated proteins are located in lanes 5, 6, 7, and 8. In FIG. 12, lanes 2–6 contain samples from foot rot, healthy, psorosis, and healthy, respectively, with no CBLP-positive antibodies in the area of the band of the positive blight control (lane 8).

Figure 13:
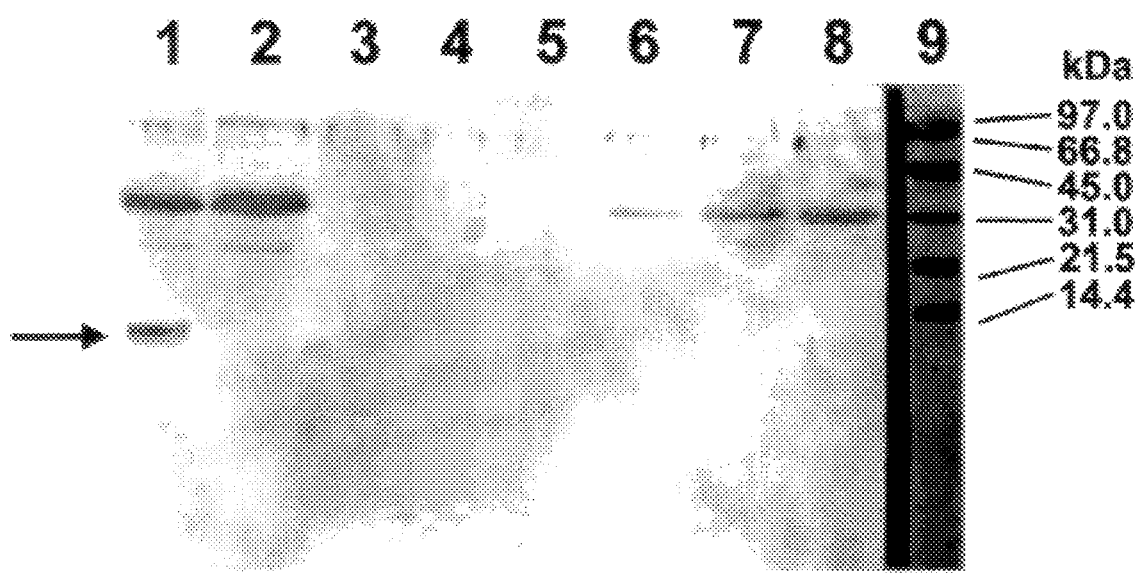

The weak positive blight band in lane 7 resulted from a sample which was visually diagnosed as affected by Rio Grande gummosis, but Zn analysis confirmed blight. Lane 9 is an example of a blight positive antibody reaction in a 20-yr-old Marsh grapefruit tree. The antibody to citrus blight-associated proteins did not cross react with *Xylella fastidiosa* (Pierce's Disease). Diagnosis B was negative for Xylella-inoculated Hamlin orange tree, and a vinifera grape variety Caignane (FIG. 13) infected with Pierce's Disease (lane 3) or extract from healthy grape (lane 4). None of the Pierce's Disease inoculated (lanes 5, 6) and healthy (lanes 7, 9) citrus plants in the area below the lysozyme (14.4 kDa) marker gave a reaction. Lane 1 contains the blight positive control and lane 2 a negative healthy control.

TABLE 2

Comparison of the methods of diagnosis currently in use for citrus blight and the Western Blot technique with citrus blight-associated protein antibody. V = visual diagnosis for the presence of a disease, W = water injection, Z = wood zinc analysis, H = Healthy, B = citrus blight, + = Western Blot positive, − = Western Blot negative.

| | Description | Diagnosis A | Diagnosis B |
|---|---|---|---|
| | Greenhouse sources | | |
| 1. | Rough Lemon (RL) citrus yellow shoot | V | − |
| 2. | Grapefruit (RL) citrus yellow shoot | V | − |
| 3. | Grapefruit likubin LK5 | V | − |
| 4. | Rough lemon likubin LK5 | V | − |
| 5. | Grapefruit South African Greening | V | − |
| 6. | Rough Lemon South African Greening | V | − |
| 7. | Rough lemon R1 Reunion | V | − |
| 8. | Grapefruit R1 R1B Reunion | V | − |
| 9. | Grapefruit B1b Reunion | V | − |
| 10. | Citron Gummy Bark (Turkey) | V | − |
| 11. | Citron Psorosis (India) | V | − |
| 12. | Citrus variegation virus CVV7ARMA861 | V | − |
| 13. | Citrus variegation virus CVVRMA861 | V | − |
| 14. | Citron Tatter Leaf | V TL-CSV-5A | − |
| 15. | Exocortis E 131 RL | V | − |
| 16. | Phytophthora M96 | V | − |
| 17. | Phytophthora T-17 | V | − |
| 18. | Citrus leaf rugose CLR-V2-RMA861 | V | − |
| 19. | Algerian navel virus | V | − |
| 20. | Tatterleaf (FS45)TLC | V | − |
| 21. | Tristeza | Serology | − |
| 22. | Water stress Valencia/RL 3 trees | Scholander pressure bomb (SPB) (−2.5 MPa) | − |
| 23. | Water stress Hamlin/RL 3 trees | SPB (−2.4 MPa) | − |

TABLE 2-continued

Comparison of the methods of diagnosis currently in use for citrus blight and the Western Blot technique with citrus blight-associated protein antibody. V = visual diagnosis for the presence of a disease, W = water injection, Z = wood zinc analysis, H = Healthy, B = citrus blight, + = Western Blot positive, − = Western Blot negative.

| | Description | Diagnosis A | Diagnosis B |
|---|---|---|---|
| 24. | Water stress Valencia/Cleo 3 trees | SPB (−2.2 MPa) (5 days) | − |
| | | St. Cloud 3/30/90 | |
| 25. | Hamlin/RL (20 yrs) 5-3 | B, V, W, Z | + |
| 26. | Hamlin/RL (20 yrs) 7-39 | B, V, W, Z | + |
| 27. | Hamlin/RL (20 yrs) 1-43 | B, V, W, Z | + |
| 28. | Hamlin/RL (20 yrs) 2-20 | B, V, W, Z | + |
| 29. | Hamlin/RL (20 yrs) 4-25 | B, V, W, Z | + |
| 30. | Hamlin/RL (20 yrs) 3-35 | B, V, W, Z | + |
| 31. | Hamlin/RL (20 yrs) 4-37 | H, V, W, Z | − |
| 32. | Hamlin/RL (20 yrs) 3-34 | B, V, W, Z | + |
| 33. | Hamlin/RL (20 yrs) 11-10 | B, V, W, Z | + |
| 34. | Hamlin/RL (20 yrs) 20-1 | H, V, W, Z | − |
| 35. | Hamlin/RL (46 yrs) 5-1 | B, V, W, Z | + |
| 36. | Hamlin/RL (46 yrs) 9-3 | H, V, W, Z | − |
| 37. | Hamlin/RL (46 yrs) 9-5 | H, V, W, Z | − |
| 38. | Hamlin/RL (46 yrs) 10-4 | H, V, W, Z | − |
| 39. | Hamlin/RL (46 yrs) 11-2 | H, V, W, Z | − |
| 40. | Hamlin/RL (46 yrs) 11-3 | H, V, W, Z | − |
| 41. | Hamlin/RL (46 yrs) 10-1 | B, V, W, Z | + |
| 42. | Hamlin/RL (46 yrs) 37-3 | H, V, W, Z | − |
| 43. | Hamlin/RL (46 yrs) 36-5 | H, V, W, Z | − |
| 44. | Hamlin/RL (46 yrs) 35-6 | H, V, W, Z | − |
| | | St. Cloud 4/27/90 | |
| 45. | Hamlin/RL (20 yrs) | B, V, W, Z | + |
| 46. | Hamlin/RL (20 yrs) | B, V, W, Z | + |
| 47. | Hamlin/RL (20 yrs) | B, V, W, Z | + |
| 48. | Hamlin/RL (20 yrs) | B, V, W, Z | + |
| 49. | Hamlin/RL (20 yrs) | H, V, W, Z | − |
| 50. | Hamlin/RL (20 yrs) | H, V, W, Z | − |
| 51. | Hamlin/RL (20 yrs) | H, V, W, Z | − |
| 52. | Hamlin/RL (20 yrs) | H, V, W, Z | − |
| 53. | Hamlin/RL (20 yrs) | H, V, W, Z | − |
| 54. | Hamlin/RL (20 yrs) | H, V, W, Z | + |
| | | Arcadia (4/27/90) | |
| 55. | Valencia/RL 3-13 | B, V, W, Z | + |
| 56. | Valencia/RL 2-6 | B, V, W, Z | + |
| 57. | Valencia/RL 4-14 | H, V, | − |
| 58. | Valencia/RL 2-16 | B, V | + |
| 59. | Valencia/RL 3-25 | H, V | − |
| 60. | Valencia/RL 8-28 | B, V, W, Z | + |
| 61. | Valencia/RL 7-24 | B, V, W, Z | + |
| 62. | Valencia/RL 8-9 | H, V | + |
| 63. | Valencia/RL 11-27 | B, V | + |
| 64. | Valencia/RL 14-30 | H, V | − |
| 65. | Valencia/RL 13-30 | H, V | − |
| 66. | Valencia/RL 15-26 | B, V, W, Z | + |
| 67. | Valencia/RL 15-21 | H, V | − |
| 68. | Valencia/RL 14-13 | B, V, W, Z | + |
| 69. | Valencia/RL 20-3 | B, V, W, Z | + |
| 70. | Valencia/RL 19-12 | H, V, W, Z | − |
| 71. | Valencia/RL 20-12 | H, V, W, Z | − |
| 72. | Valencia/RL 20-5 | H, V, | − |
| 73. | Valencia/RL 18-19 | B, V, W, Z | + |
| 74. | Valencia/RL 21-3 | H, V, W, Z | − |
| | | St. Cloud 5/7/90 | |
| 75. | Romosassa/Carrizo | B, V, W | + |
| 76. | Red Blood/Carrizo | B, V, W | + |
| 77. | Romosassa/Carrizo | H, V, W | − |
| 78. | Mediterranean Sweet/Carrizo | H, V, W | − |
| 79. | Pera/Carrizo | B, V, W, Z | + |
| 80. | Pera/Carrizo | H, V, W, Z | − |
| | | Ft. Pierce 5/30/90 | |
| 81. | Val/RL 40 yrs | B, V, W, Z | + |
| 82. | Val/RL 40 yrs | B, V, W, Z | + |

TABLE 2-continued

Comparison of the methods of diagnosis currently in use for citrus blight and the Western Blot technique with citrus blight-associated protein antibody. V = visual diagnosis for the presence of a disease, W = water injection, Z = wood zinc analysis, H = Healthy, B = citrus blight, + = Western Blot positive, − = Western Blot negative.

|  | Description | Diagnosis A | Diagnosis B |
|---|---|---|---|
| 83. | Val/RL 40 yrs | H, V, W, Z | − |
| 84. | Exocortis Val/Trif 40 yrs | H, V, W, Z | − |
| 85. | Val/Trif 40 yrs | H, V, W, Z | − |
| 86. | CTV severe Val/ sour 40 yrs | H, V, W, Z | − |
| 87. | Pine/Cleo 30 yrs | B, V, W | + |
| 88. | Pine/Cleo 30 yrs | B, V, W | + |
| 89. | Healthy 30 yrs | H, V, W, Z | − |
| 90. | Navel/Carrizo 9 yrs | B, V, W, Z (15 ppm) | + |
| 91. | Navel/Carrizo 9 yrs | H, V, W, Z (17 ppm) | + |
| 92. | CTV Marsh/Sour 9 yrs | H, V, W, Z | − |
| 93. | Marsh/Sour 9 yrs | H, V, W, Z | − |
| 94. | Exocortis Ruby/Rangpur 10 yrs | H, V, W, Z | − |
| 95. | Exocortis Ruby/Rangpur 10 yrs | H, V, W, Z | − |
| 96. | Xyloporosis Val/tangelo 30 yr | H, V, W, Z | − |
| 97. | Xyloporosis Val/tangelo 30 yrs | H, V, W, Z | − |
| 98. | Xyloporosis Val/tangelo 30 yrs | H, V, W, Z | − |
| 99. | Phytophthora Val/RL 5 yr | H, V, W, Z | − |
| 100. | Phytophthora Val/RL 5 yr | H, V, W, Z | − |
| 101. | Val/RL | H, V, W, Z | − |
| 102. | Psorosis Temple/Cleo 35 yr | H, V, W, Z | − |
| 103. | Psorosis Temple/Cleo 35 yr | H, V, W, Z | − |
| 104. | Temple/Cleo 35 yrs | H, V, W, Z | − |
| 105. | Rio Grande Gummosis + Water Marsh/Carr 20 yr | B, V, W, Z | + |
| 106. | Water Stress Marsh/Carr 20 yr | B, V, W, Z | + |
| 107. | Marsh/Rangpur 20 | H, V, W, Z | − |
| 108. | Water Stress Pine/Trif 20 yr | H, V, W, Z | − |
| 109. | Water Stress Pine/Trif 20 yr | H, V, W, Z | − |
| 110. | Pine/Cleo 20 yr | H, V, W, Z | − |
| 111. | Rio Grande Gummosis Marsh/RL | H, V, W, Z | − |
|  | Sebring |  |  |
| 112. | Marsh/RL | H, V, W, Z | − |
| 113. | Marsh/RL | B, V, W, Z | + |
| 114. | Marsh/RL | B, V, W, Z | + |
| 115. | Marsh/RL | H, V, W, Z | − |
| 116. | Marsh/RL | B, V, W, Z | + |
| 117. | Redblush/Carr | B, V, W, Z | + |
| 118. | Redblush/Carr | B, V, W, Z | + |
| 119. | Marsh/Carr | B, V, W, Z | + |
| 120. | Marsh/Carr | B, V, W, Z | + |
| 121. | Marsh/Carr | B, V, W, Z | + |
|  | Avon Park |  |  |
| 122. thru 127. | Navel/Carr Citrus Nematode (Radolpolus citrophilla Huttal, Dixon, Kaplan) 6 trees | H, V, W, Z | −? |
| 128. thru 135. | Navel/Carr 6 trees Greenhouse, Orlando | H, V, W, Z | − |
| 136. thru 138. | Sour/orange (Radolpolus citrophilla infested) 3 trees | V | − |
| 139. thru 142. | Sour/orange (healthy) | V | − |

The advantage of this test system in diagnosing blight in trees with multiple diseases is evidenced by the case where Rio Grande Gummosis (sample 105) was present in addition to blight (confirmed by elevated Zn levels). It was antibody positive while another tree having only Rio Grande gummosis (tree no. 111) was antibody negative.

The detection of the protein complex in the 12–13 kDa region is highly correlated with citrus blight. The results obtained in this study show that test can be used to differentiate citrus blight from other diseases and disorders. Blight was detected in the absence of reliable visual symptoms.. The results in Table 2 are based on a blind test of the immunological test against established procedures.

EXAMPLE XII

Oligonucleotide Probes

The amino acid sequences in Example VIII for the proteins SEQ ID NO. 1, SEQ ID NO. 2 and SEQ ID NO. 3 are used to generate specific oligonucleotides to be used as probes in diagnostic techniques and to further isolate and characterize the nucleotide coding sequence.

Degenerative oligonucleotides are made from the specific amino acid sequences. These are labeled and used to probe cDNA libraries formed from citrus blight leaf and healthy citrus leaf.

Oligonucleotide primers are also made from the specific amino acid sequences. The oligonucleotide primers made to terminal portions of the amino acid sequence are used to amplify Poly (A) mRNA and produce a probe complementary to the coding region of the blight protein genes.

The diagnostic probes are used in conjunction with Northern blots of the expressed genes to determine if the specific blight protein is present in the citrus genes.

Molecular Cloning: A Laboratory Manual Vol:1–3, Eds, Sambrook, J. et al (1989) Cold Spring Harbor Laboratory Press and Nishizawa, Y. et al, *Plant Sci.* 76:211–218 (1991), both incorporated herein by reference.

The foregoing description of the specific embodiments reveals the general nature of the invention and others can by applying current knowledge, readily modify and/or adapt such specific embodiments without departing from the inventive concept and therefore such adaptations and modifications should be and are intended to be comprehended within the meaning and range of equivalents of the disclosed embodiments. It is to be understood that the phraseology or terminology employed herein is for purposes of description and not of limitation.

What is claimed is:

1. An isolated and purified citrus blight leaf protein, extracted from citrus blighted leaves, having a molecular weight of about 12,500 to about 13,000 daltons using sodium dodecyl sulfate polyacrylamide gel electrophoresis and a partial amino acid sequence selected from the group consisting of and SEQ ID NO. 2 and SEQ ID NO. 3.

2. An isolated and purified citrus blight leaf protein according to claim 1 having a partial amino acid sequence as set forth in SEQ ID NO. 2 and wherein Val is valine, Asn is asparagine, Ala is alanine, Ileu is Isoleucine, Thr is threonine, Gly is glycine, Arg is arginine, Lys is lysine, and Ser serine.

3. An isolated and purified citrus blight leaf protein according to claim 1 having a partial amino acid sequence as set forth in SEQ ID NO. 3 and wherein Val is valine, Leu is leucine, Gly is glycine, Gln is glutamine, Ala is alanine, Thr is threonine, Phe is phenylalanine, Tyr is tyrosine, Asn is asparagine, and Pro is proline.

4. An antigen composition prepared from a 12,500–13,000 dalton molecular weight fraction of isolated and purified citrus blight leaf protein sufficient to elicit an antibody immunoreactive with a citrus blight leaf protein according to claim 1.

5. An antigen composition prepared from a 12,500–13,000 dalton molecular weight fraction of isolated and purified citrus blight leaf protein sufficient to elicit an antibody immunoreactive with a citrus blight leaf protein according to claim 2.

6. An antigen composition prepared from a 12,500–13,000 dalton molecular weight fraction of isolated and purified citrus blight leaf protein sufficient to elicit an antibody immunoreactive with a citrus blight leaf protein according to claim 3.

7. An antigen composition prepared from a 12,000–13,000 dalton molecular weight fraction of isolated and purified citrus blight leaf protein according to claim 1 by the steps of:

A) electrocuting said antigen from electrophoretic gels encompassing protein from about 12,500 to about 13,000 dalton in molecular weight;

B) purifying said antigen on an affinity column effective for binding said proteins; and C) dialyzing said antigen to remove impurities.

8. An antibody for distinguishing a citrus blight leaf protein wherein said antibody specifically binds a citrus blight leaf protein of claim 1 within said 12,500–13,000 dalton range, but is immunologically non-reactive with blight-free leaf proteins within said range.

9. An antibody for distinguishing a citrus blight leaf protein wherein said antibody specifically bind a citrus blight leaf protein of claim 7 within said 12,500–13,000 dalton range, but is immunologically non-reactive with blight-free leaf proteins within said range.

10. An antibody for distinguishing a citrus blight leaf protein wherein said antibody specifically binds a citrus blight leaf protein of claim 8 within said 12,500–13,000 dalton range, but is immunologically non-reactive with blight-free leaf proteins within said range.

11. The antibody of claim 8 wherein IgG of said antibody is removed by agarose-bound recombinant Protein A.

12. The antibody of claim 8 wherein IgG of said antibody is removed by agarose-bound recombinant Protein G.

* * * * *